United States Patent
Sharma et al.

(10) Patent No.: US 10,287,259 B2
(45) Date of Patent: May 14, 2019

(54) SELENAZOLIDINE AND THIAZOLIDINE COMPOUNDS FOR TREATING CANCER AND OTHER DISEASES

(71) Applicant: The Penn State Research Foundation, University Park, PA (US)

(72) Inventors: Arun K. Sharma, Hummelstown, PA (US); Shantu Amin, Union City, NJ (US); Daniel Plano, Navarra (ES); Deepkamal Karelia, Harrisburg, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 51 days.

(21) Appl. No.: 15/457,587

(22) Filed: Mar. 13, 2017

(65) Prior Publication Data
US 2017/0260151 A1    Sep. 14, 2017

Related U.S. Application Data

(60) Provisional application No. 62/307,923, filed on Mar. 14, 2016.

(51) Int. Cl.
| | |
|---|---|
| *A61K 31/41* | (2006.01) |
| *A61K 45/06* | (2006.01) |
| *A61K 31/426* | (2006.01) |
| *C07D 277/18* | (2006.01) |
| *C07D 293/06* | (2006.01) |
| *A61K 31/7068* | (2006.01) |

(52) U.S. Cl.
CPC ............ *C07D 293/06* (2013.01); *A61K 31/41* (2013.01); *A61K 31/426* (2013.01); *A61K 31/7068* (2013.01); *A61K 45/06* (2013.01); *C07D 277/18* (2013.01)

(58) Field of Classification Search
CPC ........................... C07D 277/18; C07D 293/06
See application file for complete search history.

(56) References Cited

U.S. PATENT DOCUMENTS

| 4,183,739 A | 1/1980 | Nusslein et al. |
| 6,762,200 B2 | 7/2004 | Takagi et al. |
| 2004/0019037 A1 | 1/2004 | Askew et al. |
| 2004/0220244 A1 | 11/2004 | Takagi et al. |
| 2007/0244175 A1 | 10/2007 | Beelman et al. |
| 2010/0093814 A1 | 4/2010 | Florjancic et al. |
| 2014/0212475 A1 | 7/2014 | Robertson et al. |

FOREIGN PATENT DOCUMENTS

| JP | 63203672 A | * | 8/1988 | ........... C07D 277/04 |

OTHER PUBLICATIONS

PubChem; https://pubchem.ncbi.nlm.nih.gov/compound/12440402; "Compound Summary for CID 12440402".
PubChem; https://pubchem.ncbi.nlm.nih.gov/compound/1478062; "Compound Summary for CID 1478062".
PubChem; https://pubchem.ncbi.nlm.nih.gov/compound/389170; "Compound Summary for CID 389170".
PubChem; https://pubchem.ncbi.nlm.nih.gov/compound/3756727; "Compound Summary for CID 3756727".
PubChem; https://pubchem.ncbi.nlm.nih.gov/compound/50878417; "Compound Summary for CID 50878417".
PubChem; https://pubchem.ncbi.nlm.nih.gov/compound/952223; "Compound Summary for CID 952223".
Chintala et al., 2010, Se-methylselenocysteine sensitizes hypoxic tumor cells to irinotecan by targeting hypoxia-inducible factor 1α, Cancer Chemother. Pharmacol. 66:899-911.
Chung et al., 2011, Melanoma Prevention Using Topical PBISe Cancer Prev. Res. 4:935-948.
Dovizio et al., 2012, Mechanistic and Pharmacological Issues of Aspirin as an Anticancer Agent, Pharmaceuticals 5:1346-1371.
Fiorucci et al., 2007, Enhanced activity of a hydrogen sulphide-releasing derivative of mesalamine (ATB-429) in a mouse model of colitis, Br. J. Pharmacol. 150:996-1002.
Gasparaian et al., 2002, Selenium Compounds Inhibit IκB Kinase (IKK) and Nuclear Factor-κB (NF-κB) in Prostate Cancer Cells, Mol. Cancer Ther. 1:1079-1087.
Gowda et al., 2013, Simultaneous Targeting of COX-2 and AKT Using Selenocoxib-1-GSH to Inhibit Melanoma, Mol. Cancer Ther. 12:3-15.
Hu et al., 2008, Methylseleninic Acid Enhances Taxane Drug Efficacy against Human Prostate Cancer and Down-Regulates Antiapoptotic Proteins Bcl-XL and Survivin, Clin. Cancer Res. 14:1150-1158.
Martins et al., 2013, Synthesis and Biological Activity of 6-Selenocaffeine: Potential Modulator of Chemotherapeutic Drugs in Breast Cancer Cells, Molecules 18:5251-5264.
Misra et al., 2015, Redox-Active Selenium Compounds—From Toxicity and Cell Death to Cancer Treatment, Nutrients 7:3536-3556.
Sanmartin et al., 2012, Selenium Compounds, Apoptosis and Other Types of Cell Death: An Overview for Cancer Therapy, Int. J. Mol. Sci. 13:9649-9672.
Schumacker, 2006, Reactive oxygen species in cancer cells: Live by the sword, die by the sword, Cancer Cell 10:175-176.
Tan et al., 2011 Aspirin, nonsteroidal anti-inflammatory drugs (NSAID), acetaminophen, and pancreatic cancer risk: A clinic-based case-control study, Cancer Prev. Res. 4:1835-1841.
Tanaka et al., 2014, Nitrogen Oxide-Releasing Aspirin Induces Histone H2AX Phosphorylation, ATM Activation and Apoptosis Preferentially in S-Phase Cells: Involvement of Reactive Oxygen Species, Cell Cycle 5:1669-1674.

(Continued)

*Primary Examiner* — Joseph R Kosack
(74) *Attorney, Agent, or Firm* — Riverside Law LLP

(57) ABSTRACT

The present invention includes compounds useful in preventing or treating cancer in a subject in need thereof. The present invention also includes methods of preventing or treating cancer in a subject in need thereof by administering to the subject a therapeutically effective amount of a compound of the invention.

6 Claims, 18 Drawing Sheets

(56) References Cited

OTHER PUBLICATIONS

Li et al., 2009 Combination of methylselenocysteine with tamoxifen inhibits MCF-7 breast cancer xenografts in nude mice through elevated apoptosis and reduced angiogenesis, Breast Cancer Res. Treat 118:33-43.

Drew et al., 2016, Aspirin and colorectal cancer: the promise of precision chemoprevention, Nature Reviews Cancer 16:173-186.

Cui et al., 2014, High-Dose Aspirin Consumption Contributes to Decreased Risk for Pancreatic Cancer in a Systematic Review and Meta-analysis, Pancreas 43:135-140.

Alcolea et al., 2012, Novel seleno- and thio-urea derivatives with potent in vitro activities against several cancer cell lines, Eur. J. Med. Chem. 113:134-144.

Ding et al., 2014, Preparation and biological evaluation of a novel selenium-containing exopolysaccharide from *Rhizobium* sp. N613, Carbohydr. Polym. 109:28-34.

Plano et al., 2016, Design, Synthesis, and Biological Evaluation of Novel Selenium (Se-NSAID) Molecules as Anticancer Agents, J. Med. Chem. 59, 1946-1959.

Lin et al., 2011, Seleno-cyclodextrin sensitises human breast cancer cells to TRAIL-induced apoptosis through DR5 induction and NF-jB suppression, Eur. J. Cancer 47:1890-1907.

Kopp and Ghosh, 1994, Inhibition of NF-κB by Sodium Salicylate and Aspirin, Science 265:956-959.

\* cited by examiner

SELENAZOLIDINE AND THIAZOLIDINE COMPOUNDS FOR TREATING CANCER AND OTHER DISEASES

CROSS-REFERENCE TO RELATED APPLICATIONS

The present application claims priority to U.S. Provisional Application No. 62/307,923, filed Mar. 14, 2016, which is hereby incorporated by reference in its entirety herein.

BACKGROUND OF THE INVENTION

Patients with pancreatic cancer (PC) have a median survival of only 6 months and a five-year survival of less than 5%, hence making PC one of the deadliest cancer (Klein et al., 2013, Nat. Rev. Cancer 13:66-74; Howlander et al., SEER Cancer Statistics Review, 1975-2009 (Vintage 2009 Populations) Online Data—http://seer.cancer.gov/csr/1975_2009_pops09/index.html). Severity of PC is due to its identification at late stages, rapid local invasion, early metastases, and meager response to current chemotherapeutic agents. Current therapies result in minimal survival advantage and are linked with multiple adverse events and drug resistance. Hence, there is an urgent need for novel agents which are less toxic and offer greater benefits over conventional therapy.

Pancreatic ductal adenocarcinoma comprises greater than 90% of PC (Samuel and Hudson, 2012, Nat. Rev. Gastroenterol. Hepatol. 9:77-87). Poor prognosis and disease stage at diagnosis contributes to low survival rate (Iovanna et al., 2012, Frontiers in Oncology:2). Chemotherapy remains the current standard of care for advanced PC patients, which include gemcitabine alone or in combination with erlotinib or a highly toxic regimen FOLFIRINOX (oxaliplatin, irinotecan, fluorouracil, and leucovorin) (Klein et al., 2013, Nat. Rev. Cancer 13:66-74; Moore et al., 2007, J. Clin. Oncol. 25:1960-1966). The current standard of care only improves survival rate on average by 6 months, but is associated with poor quality of life due to high toxicity. Molecular and cellular heterogeneity of PC tumors contribute to resistance to current standard of chemotherapy (Samuel and Hudson, 2012, Nat. Rev. Gastroenterol. Hepatol. 9:77-87). Therefore, there is an urgent need to develop novel approaches to battle metastatic PC.

Many signaling pathways have been suggested to be associated with chemo-resistance, including NF-κB, PI3k-Akt and NOTCH pathways in cancer, (Zhou et al., 2014, AAPS J. 16:246-257; Long et al., 2011, Expert Opin. Ther. Targets 15:817-818; Arlt et al., 2003, Oncogene 22:3243-3251; Wang et al., Nat. Rev. Gastroenterol. Hepatol. 8:27-33); however, chemo-resistance in PC has mainly been associated with aberrant activation of the NF-κB pathway (Arlt et al., 2012, Oncogenesis 1:e35). Further, the NF-κB pathway has been known to be induced in presence of chemotherapeutic drugs as well as radiation in PC cells 9 Arlt et al., 2003, Oncogene 22:3243-3251; Brach et al., 1991, J. Clin. Invest. 88:691-695; Bharti and Aggarwal, 2002, Biochem. Pharmacol. 64:883-888), hence making this pathway one of the hot targets for combinational treatments with current drugs in the clinic (Arlt et al., 2012, Oncogenesis 1:e35; Carbone and Melisi, Expert Opin. Ther. Targets 16 Suppl. 2:S1-S10; Ullenhag et al., 2015, PLoS One 10:e03121197; Infante et al., 2011, Eur. J. Cancer 47:199-205). The mammalian transcription factor NF-κB is formed by homo- or hetero-protein dimer complex of Rel-family proteins (Gilmore, 2006, Oncogene 25:6680-6684). The most abundant form of NF-κB exists in the form of heterodimer consisting of RelA (also known as p65) and p50 complex. The RelA and p50 NF-κB complex is inhibited in the cytoplasm from entering the nucleus by inhibitor of κB proteins (IκBα). In classical activation of NF-κB pathway, upon inflammatory stimuli (like TNF-α), downstream IκB kinase complex (IKK), which is made up of two catalytic kinases (IKKα and IKKβ) and a regulatory component IKKγ, is activated via phosphorylation (Gilmore, 2006, Oncogene 25:6680-6684). Upon activation of IKK, IKK phosphorylates IκBα. Phosphorylated IκBα is polyubiquitnated and degraded, hence RelA and p50 complex can freely localize to the nucleus and interact with their corresponding gene targets. Upon activation, NF-κB upregulates the transcription of anti-apoptotic proteins (like Blc-2, Bcl-xL, Mcl-1, etc), proliferative proteins (cyclin D), proteins involved in cell invasion (VEGF, MMPS, etc.) and pro-inflammatory cytokines (TNF-α, and different interleukins) (Gilmore, 2006, Oncogene 25:6680-6684).

Over the past decade, NSAIDs have emerged as potent chemopreventive agents (Streicher et al., 2014, Cancer Epidemiology Biomarkers & Prevention 23:1254-1263; Tan et al., Cancer Prev. Res. 4:1835-1841; Bonifazi et al., 2010, Eur. J. Cancer Prev. 19:352-354; Chan et al., 2007, Arch. Intern. Med. 167:562-572; Agrawal and Fentiman, 2008, Int. J. Clin. Pract 62:444-449; Johannesdottir et al., 2012, Cancer 118:4768-4776; Seshasi et al., 2012, Arc. Intern. Med. 172:209-216; Trabert et al., 2014, J. natl. Cancer Inst. 106:djt431). Out of all the NSAIDs, aspirin (ASA) has received more attention for its chemopreventive ability in different cancers, specifically colorectal cancer (Rothwell, 2013, Recent Results Cancer Res. 191:121-142; Drew et al., 2016, Nature Reviews Cancer; 16:173-186). Further, there have been different clinical trials showing ASA to be clinically effective in reducing PC growth Streicher et al., 2014, Cancer Epidemiology Biomarkers & Prevention 23:1254-1263; Tan et al., Cancer Prev. Res. 4:1835-1841; Bonifazi et al., 2010, Eur. J. Cancer Prev. 19:352-354). Recent clinical studies showed that high ASA decreased PC incidence (Cui et al., 2014, Pancreas 43:135-140), however high doses or long term usage of ASA are also related to gastrointestinal (GI) toxicity (Toruner, 2007, Anadolu Kardiyol Derg, 7 Suppl 2: 27-30; Yeomans et al., 2009, Curr. Med. Res. Opin. 25:2785-2793). Hence, efforts have been made by different research groups to optimize ASA structure for improving its potency and ultimately reducing its toxicities (Drew et al., 2016, Nature Reviews Cancer; 16:173-186; Huang et al., 2011, J. Med. Chem. 54:1356-1364; Plano et al., 2016, J. Med. Chem. 56:1946-1959; Fiorucci et al., 2007, Br. J. Pharmacol. 150:996-1002; Basudhar et al., 2013, J. Med. Chem. 56:7804-7820).

Interest in designing selenium containing small molecules intensified after the link between selenium and cancer prevention strengthened based on preclinical, epidemiological and clinical investigations (Plano et al., 2016, J. Med. Chem. 56:1946-1959; Chung et al., Cancer Prev. Res. 4:935-948; Lin et al., 2011, Eur. J. Cancer 47:1890-1907; Nguyen et al., 2011, Cancer Prev. Res. 4:248-258; Chintala et al., 2010, Cancer Chemother. Pharmacol. 66:899-911; Li et al., 2009, Breast Cancer Res. Treat. 118:33-43; Martins et al., 2013, Molecules 18:5251-5264; Qi et al., 2012, PLoS One 7:e31539; Sharma and Amin, Future Med. Chem. 5:163-174). In the recent literature, several new selenium compounds have been developed including several from our laboratories and many of them have shown promising cancer preventive and/or therapeutic activity (Plano et al., 2016, J. Med. Chem. 56:1946-1959; Sharma and Amin, Future Med.

Chem. 5:163-174; Alcolea et al., 2016, Eur. J. Med. Chem. 113:134-44; Ding et al., 2014, Carbohydr. Polym. 109:28-34; Zeng et al., 2014, Chem. Asian J. 9:2295-2302; Sharma et al., 2008, J. Med. Chem. 51:7820-7826). The mechanisms by which selenium containing molecules inhibit cancer growth differ according to the structure of the overall compound (Jackson and Combs, 2008, Curr. Opin. Clin. Nutr. Metab. Care 11:718-726). The most commonly described mechanisms by which selenium compounds exerts their anti-cancer ability are: induction of reactive oxygen species (ROS) or quenching of ROS (Plano et al., 2016, J. Med. Chem. 56:1946-1959); inhibition of different pro-survival proteins (like Bcl-xL and Survivin); induction of apoptosis; inhibition of angiogenesis; modulation of AKT, COX, p38 and NF-κB-signaling pathways (Gowda et al., 2013, Mol. Cancer Ther. 12:3-15; Sanmartin et al., 2008, Mini Rev. Med. Chem. 8:1020-1031; Sanmartin et al., 2012, Int. J. Mol. Sci. 13:9649-9672; Hu et al., 2008, Clin. Cancer Res. 14:1150-1158; Abbas and Sakr, 2013, J. Physiol. Biochem. 69:527-537).

In normal cells, the major source of ROS is mitochondria (Ray et al., 2012, Cell Signal 24:981-990). ROS are very unstable and can damage DNA and proteins (Sabharwal and Schumacker, 2014, Nat. Rev. Cancer 14:709-721). Cancer cells show high basal ROS levels because of mitochondrial activity as compared to their normal counterparts (Sabharwal and Schumacker, 2014, Nat. Rev. Cancer 14:709-721). Hence, ROS inducing agents have been proposed to kill cancer cells selectively over normal cells by increasing the amount of ROS enough to tip the balance towards cancer cell death (Schumacker, 2006, Cancer Cell 10:175-176). Drawback of the ROS inducing agents is that the cancer cells also have up-regulation of stress pathways like NF-κB (Ahn et al., 2007, Curr. Mol. Med. 7:619-637), which can upregulate not only anti-apoptotic proteins but anti-oxidant enzymes which can counter act the increased ROS levels in cancer cells (Sabharwal and Schumacker, 2014, Nat. Rev. Cancer 14:709-721; Morgan and Liu, 2011, Cell Res. 21:103-115; Reuter et al., 2010, Free Radic. Biol. Med. 49:1603-1616; Trachootham et al., 2009, Nat. Rev. Drug Discov. 8:597-591; Holstrom and Finkel, 2014, Nat. Rev. Mol. Cell. Biol. 15:411-421) Hence, it has been proposed that compounds that have dual action of increasing ROS levels and further inhibiting the NF-κB resistance pathway may play a major role in killing the cancer cells (Reuter et al., 2010, Free Radic. Biol. Med. 49:1603-1616). Further, ASA derived molecules like NO-aspirin are known to induce ROS species in cancer cells (Tanaka et al., 2014, Cell Cycle 5:1669-1674), while selenium containing compounds can either be a pro-oxidant or anti-oxidant depending on the types of active metabolites formed (Plano et al., 2016, J. Med. Chem. 1946-1959).

p21 and p27 are markers activated in the presence of DNA damage or apoptosis (Gartel and Tyner, 2002, Mol. Cancer Ther. 1:639-649; Abbas and Dutta, 2009, Nat. Rev. Cancer 9:400-414; Kastan and Bartek, 2004, Nature 432:316-323). Literature reports suggest that histone deacetylase (HDAC) inhibitors can activate p21 and p27 expression (Yang and Seto; 2007, Oncogene, 26:5310-5318; Blagosklonny et al., 2002, Mol. Cancer Ther. 1:937-941; Takai et al., 2004, Cancer 101:2760-2770). ASA also has been known to induce expression of both proteins (Marra et al., 2000, Circulation 102:2124-2130; Dikshit, 2006, J. Biol. Chem. 281:29228-29235) and could increase histone acetylation to show its effects (Passcquale et al., 2015, Br. J. Pharmacol. 172:3548-3564).

It has been demonstrated that inflammation plays a major role in PC initiation, progression and metastasis (Takahashi et al, 2013, Semin. Immunopathol. 35:203-227; Steele et al., 2013, Br. J. Cancer 108:997-1003; Marusawa and Jenkins, 2014, Cancer Lett. 345:153-156). Nuclear factor κB (NF-κB) pathway, one of the major inflammatory pathway, is well known for its inflammatory response, cell proliferation, and resistance to apoptosis. NF-κB is a major stress related pathway, and one of the targets of NF-κB are anti-oxidant proteins (Chen et al., 2007, Cancer Res. 67:1472-1486; Sullivan and Graham, 2008, Curr. Pharm. Des. 14:1113-1123). It has been demonstrated that activation of NF-κB in PC is also responsible for resistance towards first line chemotherapeutic agent, gemcitabine, in PC. Studies have suggested that the cancer cells acquire resistance to gemcitabine through aberrant activation of NF-κB pathway. Patients who show resistance to gemcitabine, have high expression of NF-κB in their tumor sites, which is correlated with less survival rates (Voutsadakis, 2011, World J. Gastrointest. Oncol. 3:153-164; Dhilon et al., 2008, Clin. Cancer Res. 14:4491-4499; Wang et al., 1999, Clin. Cancer Res. 5:119-127).

Thus, there is a need in the art to identify novel compounds which are useful for the treatment of pancreatic cancer, in addition to other diseases and disorders, and do not cause deleterious side effects in the subject. The present invention fulfills this need.

SUMMARY OF THE INVENTION

The present invention includes a compound of formula (I):

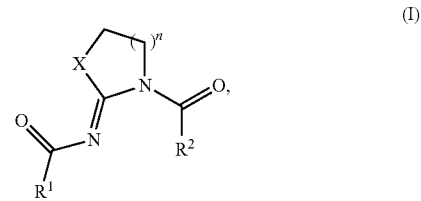

wherein in formula (I):

$R^1$ and $R^2$ are each independently selected from the group consisting of —$C_1$-$C_6$ alkyl, —$C_1$-$C_6$ fluoroalkyl, —$C_1$-$C_6$ heteroalkyl, —$OR^3$, —$SR^3$, —$C(=O)R^3$, —$OC(=O)R^3$, —$OCO_2R^3$, —$CH(R^3)_2$, —$N(R^3)_2$, —$C(OH)(R^3)_2$, —$C(NH_2)(R^3)_2$, cycloalkyl, aryl, heteroaryl, —$C_1$-$C_6$ alkyl-aryl, —$C_1$-$C_6$ alkyl-heteroaryl, —$C_1$-$C_6$ alkyl-cycloalkyl, wherein the alkyl, cycloalkyl, aryl, heteroaryl, alkylaryl, alkylheteroaryl, and alkylcycloalkyl, group may be optionally substituted;

each occurrence of $R^3$ is independently selected from the group consisting of H and —$C_1$-$C_6$ alkyl;

n is an integer between 1 and 3; and

X is selected from the group consisting of Se and S, a salt or solvate thereof, and any combinations thereof.

In one embodiment, X is Se. In one embodiment, n is 1. In another embodiment, the compound is selected from the group consisting of:

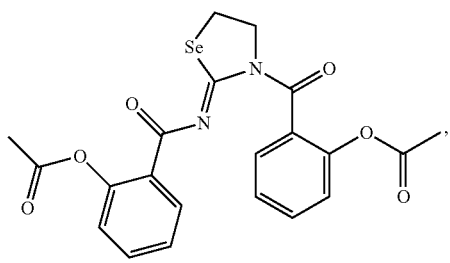 [SMILES: CC(=O)Oc1ccccc1C(=O)/N=C1\[Se]CCN1C(=O)c1ccccc1OC(C)=O]

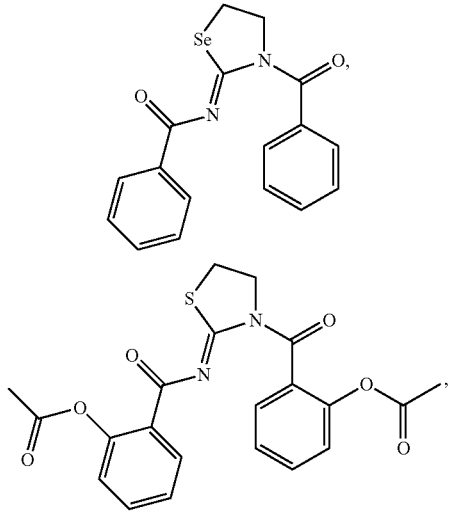

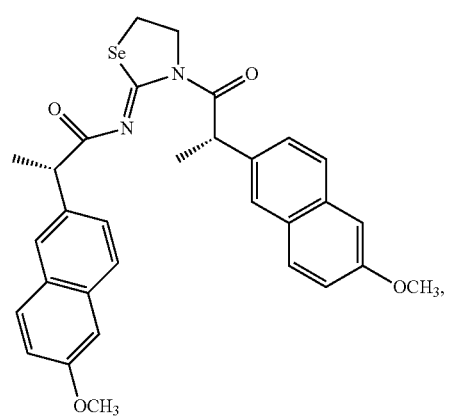

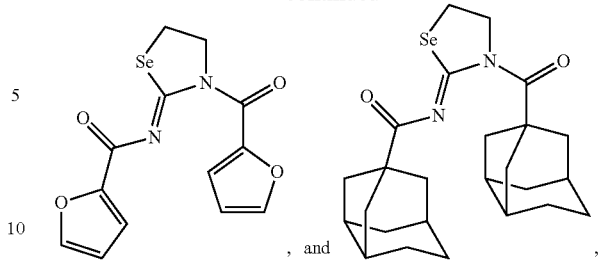

, and 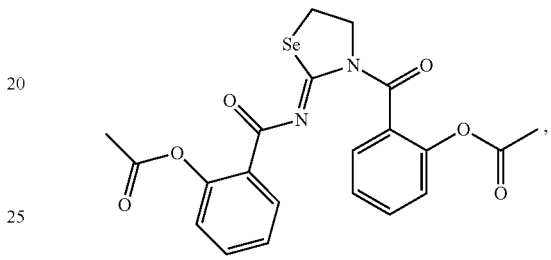, a salt or solvate thereof, and any combinations thereof. In one embodiment, the compound is:

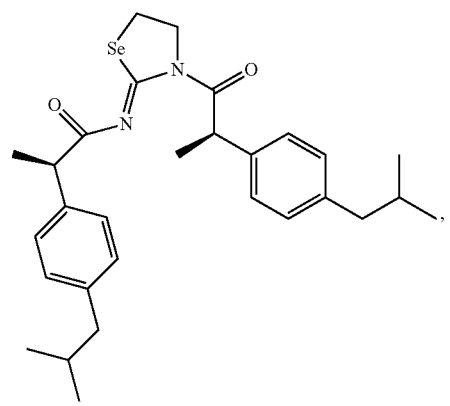

a salt or solvate thereof, and any combinations thereof.

The present invention also includes a composition comprising a compound of formula (I). In one embodiment, the composition further includes a pharmaceutically acceptable carrier. In one embodiment, the composition further includes an additional therapeutic agent. In one embodiment, the therapeutic agent is gemcitabine.

The present invention also includes a method of preventing or treating cancer in a subject in need thereof. In one embodiment, the method includes administering to the subject a therapeutically effective amount of a composition comprising at least one compound of formula (I), a salt or solvate thereof, and any combinations thereof.

In one embodiment, X is Se. In one embodiment, n is 1. In one embodiment, the compound is selected from the group consisting of:

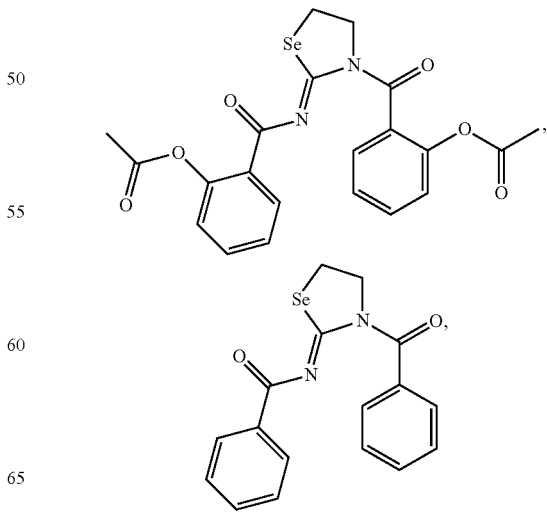

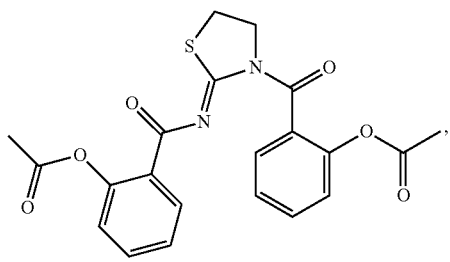

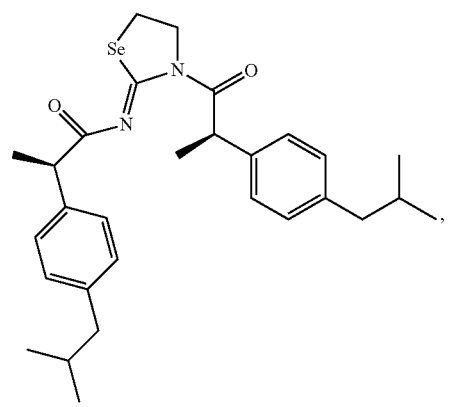

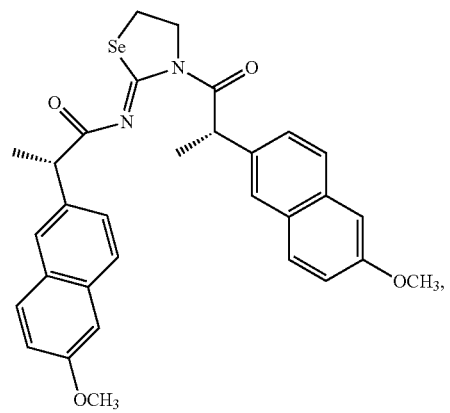

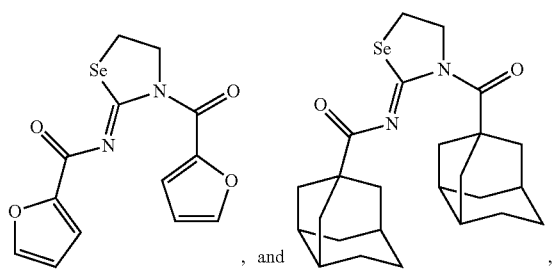 [SMILES: O=C(/N=C1\[Se]CCN1C(=O)c1ccco1)c1ccco1 ; O=C(/N=C1\[Se]CCN1C(=O)C12CC3CCC(C1)C(C3)C2)C12CC3CCC(C1)C(C3)C2]

a salt or solvate thereof, and any combinations thereof. In one embodiment, the compound is:

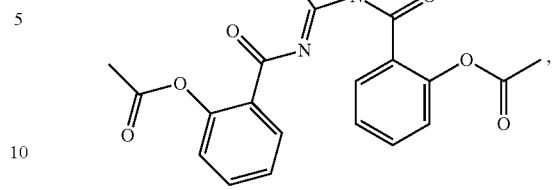

a salt or solvate thereof, and any combinations thereof. In one embodiment, the cancer is selected from the group consisting of lung cancer, colon cancer, colorectal cancer, melanoma, breast cancer, ovarian cancer, prostate cancer, liver cancer, pancreatic cancer, CNS tumors (including brain tumors), neuroblastoma, leukemia, bone cancer, intestinal cancer, lymphoma, and combinations thereof. In one embodiment, the cancer is pancreatic cancer. In one embodiment, the method further includes administering to the subject at least one additional therapeutic agent. In one embodiment, the therapeutic agent is a chemotherapeutic agent. In one embodiment, the therapeutic agent is gemcitabine. In one embodiment, the composition and the additional therapeutic agent are co-administered. In one embodiment, the composition and the additional therapeutic agent are co-formulated.

The present invention also includes a method of preventing or treating inflammation or pain in a subject in need thereof. In one embodiment, the method includes administering to the subject a therapeutically effective amount of a composition comprising at least one compound of formula (I), a salt or solvate thereof, and any combinations thereof. In one embodiment, X is Se. In one embodiment, n is 1. In one embodiment, the compound is selected from the group consisting of

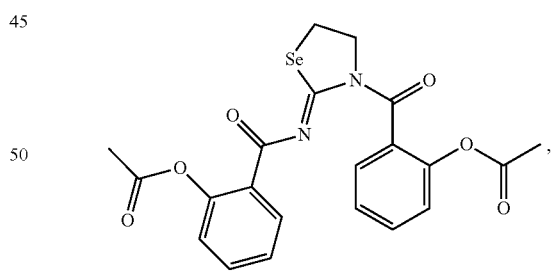

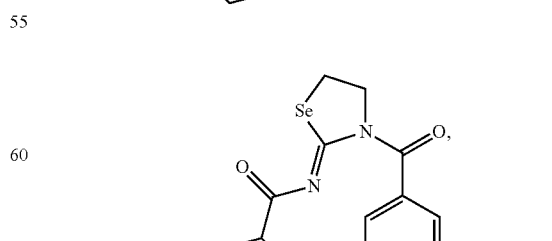

-continued

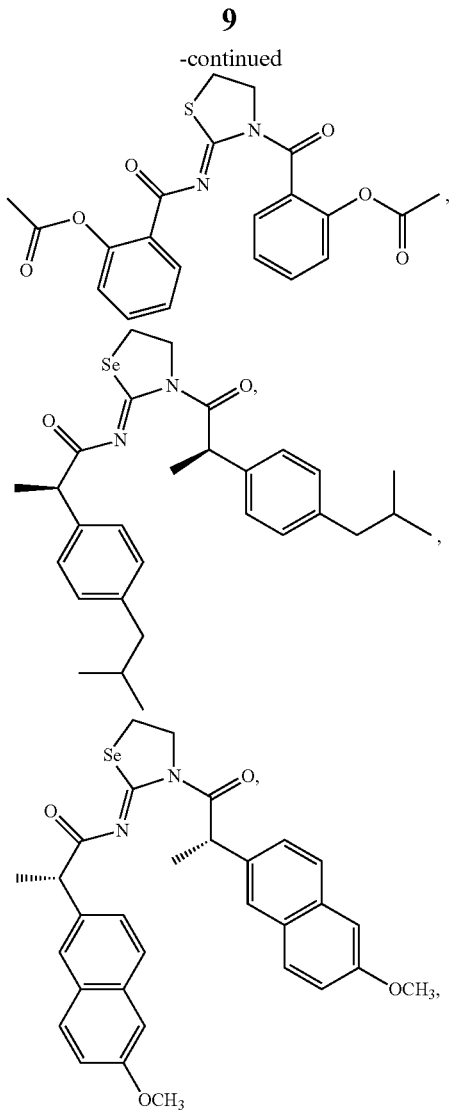

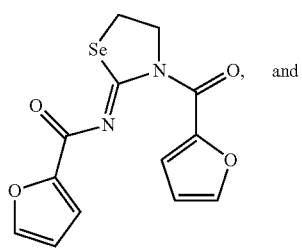

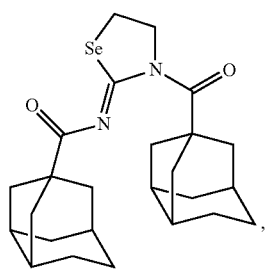

a salt or solvate thereof, and any combinations thereof. In one embodiment, the compound is:

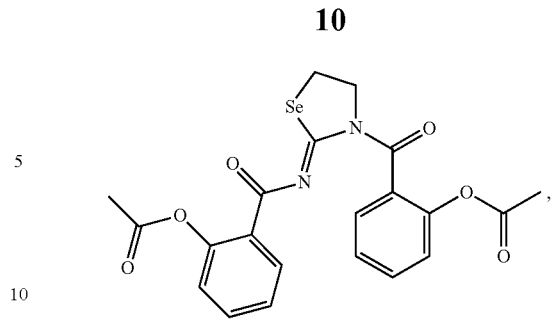

a salt or solvate thereof, and any combinations thereof. In one embodiment, the method further includes administering to the subject at least one additional therapeutic agent. In one embodiment, the therapeutic agent is a nonsteroidal anti-inflammatory drug (NSAID). In one embodiment, the composition and the additional therapeutic agent are co-administered. In one embodiment, the composition and the additional therapeutic agent are co-formulated.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 5A-5D, depicts experimental data of Panc-1 and A549 cells treated with compounds of the invention. FIG. 5A depicts the structures of the AS-10 and two AS-10 analogues, ASD-123 and ASD-171. Loss of acetyl groups or replacement of selenium by sulfur in AS-10 leads to inhibition of its anti-cancer activity. FIG. 5B depicts a table of experimental data of PC cells (Panc-1) treated for 48 h with increasing dose of AS-10. FIG. 5C depicts a table of experimental data of Lung cancer cells (A549) treated for 48 h with increasing dose of AS-10. For FIGS. 5B and 5C, the MTT assay was performed to measure cancer cell viability. Bar graph showed mean±SD. FIG. 5D is a series of images of Western blots of Panc-1 cells were treated with 10 µM AS-10 at increasing time points. At termination, whole cell lysates were subjected to Western blot analysis for monitoring the expression of acetylated histones H3 and H4. GAPDH was used as a loading control.

FIGS. 6A-6D, depicts experimental data demonstrating how AS-10 inhibits PC cell growth. FIG. 6A depicts the structure of AS-10 structure. FIG. 6B is a graph of experimental data of Panc-1 cells treated with AS-10 for 24, 48 and 72 h in a dose dependent manner. FIG. 6C is a graph of experimental data of BxPC3 cells treated with AS-10 for 24, 48 and 72 h in a dose dependent manner. Treated cells were subjected to cell viability MTT assay. Growth curves obtained by performing non-linear regression using GraphPad prism software. Data represented as mean±SD. FIG. 6D is a graph of experimental data of Panc-1 cells treated with AS-10 for 48 h. After 48 h live cells were counted and plated in new petri dish and were allowed to form colonies for 14 days. After 14 days colonies were stained with crystal violet and counted. Data represents mean±SD.

FIGS. 7A-7B, depicts experimental data demonstrating that AS-10 is more potent than Gemcitabine and selective towards cancer cells. FIG. 7A is a graph of experimental data of Panc-1 cells treated with increasing dose of AS-10 or Gemcitabine for 48 h. Cells were subjected to cell viability MTT assay at end of 48 h. FIG. 7B is a graph of experimental data of MEFs and Panc-1 cells both were treated with AS-10 for 48 h in a dose dependent manner and subjected to MTT assay. Curves in both 7A and 7B were obtained by performing non-linear regression using GraphPad Prism software. Data represents mean±SD.

FIGS. 8A-8C, depicts experimental data demonstrating that AS-10 induces G1 and G2 cells cycle arrest. Panc-1 cells were serum starved for 72 h and then treated with AS-10 for given time points. At end of each time point cells were fixed and stained with PI. Stained cells were subjected to cell cycle analysis using flow cytometry. FIG. 8A depicts a histogram showing three cell population—G1 (first peak), S (second flat peak) and G2 (last peak on the left) FIG. 8B is a graph of experimental data of the quantification of different cell cycle phases at different time points with their control respectively. FIG. 8C is a graph of experimental data of Panc-1 cells treated with 10 μM AS-10 for given time points. Whole cell lysate was subjected to Western blot analysis. Blots were probed for given proteins. β-actin was used as loading control.

FIGS. 9A-9F, depicts experimental data demonstrating that AS-10 induces intrinsic apoptosis in PC cells. FIGS. 9A and 9B depict PC cells (Panc-1) treated with AS-10 for given time points. At the end of last time point, cells were subjected to apoptosis detection using Muse caspase 3/7 activity assay and Muse Live/dead Annexin V assay. Bottom left quadrant represents healthy cells; bottom right quadrant represents early apoptotic cells (Caspase 3/7 (+), Annexin V (+) and 7-ADD (−)); top right quadrant represents late apoptotic/dead cells (Caspase 3/7 (+), Annexin V (+) and 7-ADD (+); Top left quadrant represents cells which have died of necrosis (Caspase 3/7 (−), Annexin V (−) and 7-ADD (+). FIG. 9C is a graph of experimental data representing the total apoptotic cells (early+late apoptotic cells) measured by caspase 3/7 activity assay. FIG. 9D is a graph of experimental data representing the total apoptotic cells (early+late apoptotic cells) measured by Live/dead annexin V assay. Error bars represents mean±SD. FIG. 9E is a graph of experimental data of Panc-1 cells were treated with AS-10, 10 μM, for given time points. Whole cell lysate was subjected to Western blot analysis. Resulting blots were probed for caspase 9. GAPDH was used as loading control. FIG. 9F is a graph of experimental data of Panc-1 cells were treated with different concentrations of AS-10 for 24 h. Whole cell lysates were made and subjected to Western blot analysis. Blots were probed with caspase 3 and PARP antibodies. GAPDH was used as loading control.

FIGS. 10A-10F, depicts experimental data demonstrating that AS-10 inhibits the translocation of NF-κB to the nucleus in the presence of inflammatory stimuli. FIG. 10A depicts a gel with experimental data from Panc-1 cells treated with AS-10 at indicated concentration for 6 hrs and stimulated with TNF-α (100 ng/μL) for 30 minutes. Nuclear lysates were assayed for NF-κB activation by EMSA. FIG. 10B depicts a gel with experimental data from cytosolic lysates of Panc-1 cells treated in FIG. 10A and subjected to western blot and probed with antibody against IκBα. β-actin was used as loading control. FIG. 10C depicts the results of an EMSA experiment. The NF-κB complex has p50 and p65 subunits. Nuclear lysates from TNF-α (100 ng/mL) treated cells and untreated cells were incubated with the indicated antibodies, an unlabeled NF-κB oligo or a mutant (MT) oligo probe. The resulting EMSA confirmed that the binding seen is NF-κB specific FIG. 10D is a series of images of Panc-1 cells seeded on glass coverslip and treated with AS-10 for 6 hrs and stimulated with TNF-α (100 ng/μL) for 30 minutes. Resultant cells were fixed and probed with antibody against p-65 protein (green). DAPI (blue) was used to stain the nucleus. FIG. 10E is a series of images of Panc-1 cells treated with 10 μM AS-10 for 6 hrs and subjected to live and dead analysis using calcein-AM and ethidium bromide. Green indicates live cells and red indicates dead cells. FIG. 10F depicts a series of images of a Western blot analysis: whole cell lysate was subjected to Western blot analysis and resulting blots were probed for Bcl-xL and Mcl-1; GAPDH was used as loading control.

FIGS. 11A-11E, depicts experimental data demonstrating that AS-10 potentiates the anti-cancer effects of gemcitabine towards PC cells. Panc-1 cells were treated with AS-10 and Gemcitabine (Gem) for 48 h. After 48 h cells were subjected to Muse Live/dead Annexin V assay and Live/dead calcein-AM & ethidium bromide staining. FIG. 11A is a series of histograms showing four quadrants, bottom left quadrant (Healthy cells (7-ADD (−), Annexin V (−))); bottom right quadrant (Early apoptotic (7-ADD (−), Annexin V (+))); top right quadrant (Late apoptotic/dead cells (7-ADD (+), Annexin V (+))); top left quadrant (necrotic (7-ADD (+), Annexin V (−))). FIG. 11B is a series of microscopic images of calcein-AM stained live cells (green color) and ethidium bromide stained (red color). FIG. 11C is a graph of the quantification of total apoptotic cells and total dead cells obtained from FIG. 11A. FIG. 11D is a graph of the quantification of total apoptotic cells and total dead cells obtained from FIG. 11B. Data represents mean±SD. FIG. 11E depicts a series of images of a Western blot analysis: whole cell lysate was subjected to Western blot analysis and resulting blots were probed for PARP; tubulin was used as loading control.

FIGS. 12A-12E, depicts experiments data demonstrating that AS-10's anti-apoptotic effects on PC cells were antagonized by ROS quencher, NAC. FIG. 12A is a series of graphs of experimental data of Panc-1 cells treated with DMSO, $H_2O_2$ or AS-10 for 3 and 6 h time points and subjected to Muse oxidative stress assay. M1 peak represents reactive oxygen species (ROS) negative, while M2 represents ROS positive cells. FIG. 12B is a table of experimental data of MTT assay of Panc-1 cells taken 48 h after being treated with DMSO, AS-10. NAC or in combination for 48 h. FIG. 12C is a series of light microscopy images of Panc-1 cells taken 48 h after being treated with DMSO, AS-10. NAC or in combination for 48 h. FIG. 12D is a series of graphs of Muse Caspase 3/7 activity assay of Panc-1 cells taken 48 h after being treated with DMSO, AS-10. NAC or in combination for 48 h. FIG. 12E is a series of graphs of Muse Live/dead Annexin V assay taken 48 h after being treated with DMSO, AS-10. NAC or in combination for 48 h. In FIGS. 12D and 12E, histograms show four quadrants, bottom left quadrant (Healthy cells (7-ADD (−), Annexin V (−) or Caspase 3/7 (−))); bottom right quadrant (Early apoptotic (7-ADD (−), Annexin V (+) or Caspase 3/7 (+))); top right quadrant (Late apoptotic/dead cells (7-ADD (+), Annexin V (+), Caspase 3/7 (+))); top left quadrant (necrotic (7-ADD (+), Annexin V (−), Caspase 3/7 (−))).

FIGS. 13A-13I, depicts experimental data demonstrating that AS-10 reduced cell viability of different cancer types. Cells were treated with increasing concentrations of AS-10 for 24, 48 and 72 h. Cell viability was measured using MTT assay. Data represents the mean±SD.

FIGS. 17A-17D, depicts experimental data of CRC cell growth inhibition. FIG. 17A depicts the results of an MTT assay that was performed on CRC cell lines (HT29, HCT116 and RKO) treated with increasing dose of AS-10 for 24, 48 and 72 h. Curves were obtained by performing non-linear regression analysis using variable slopes. Data represents Mean±SD. FIG. 17B depicts a flow cytometry analysis of cell cycle phases. HT29 cells were serum starved for 72 h, followed by addition of media with serum and AS-10. Cells were harvested, fixed and stained with PI. FIG. 17C depicts the quantification of the data shown in FIG. 17B. FIG. 17D is a Western blot analysis of PARP and p21 expression in whole cell lysates. HT29 cells were treated with AS-10 for 24 h in a dose dependent manner. GAPDH was used as a loading control.

DETAILED DESCRIPTION OF THE INVENTION

Figure 1:
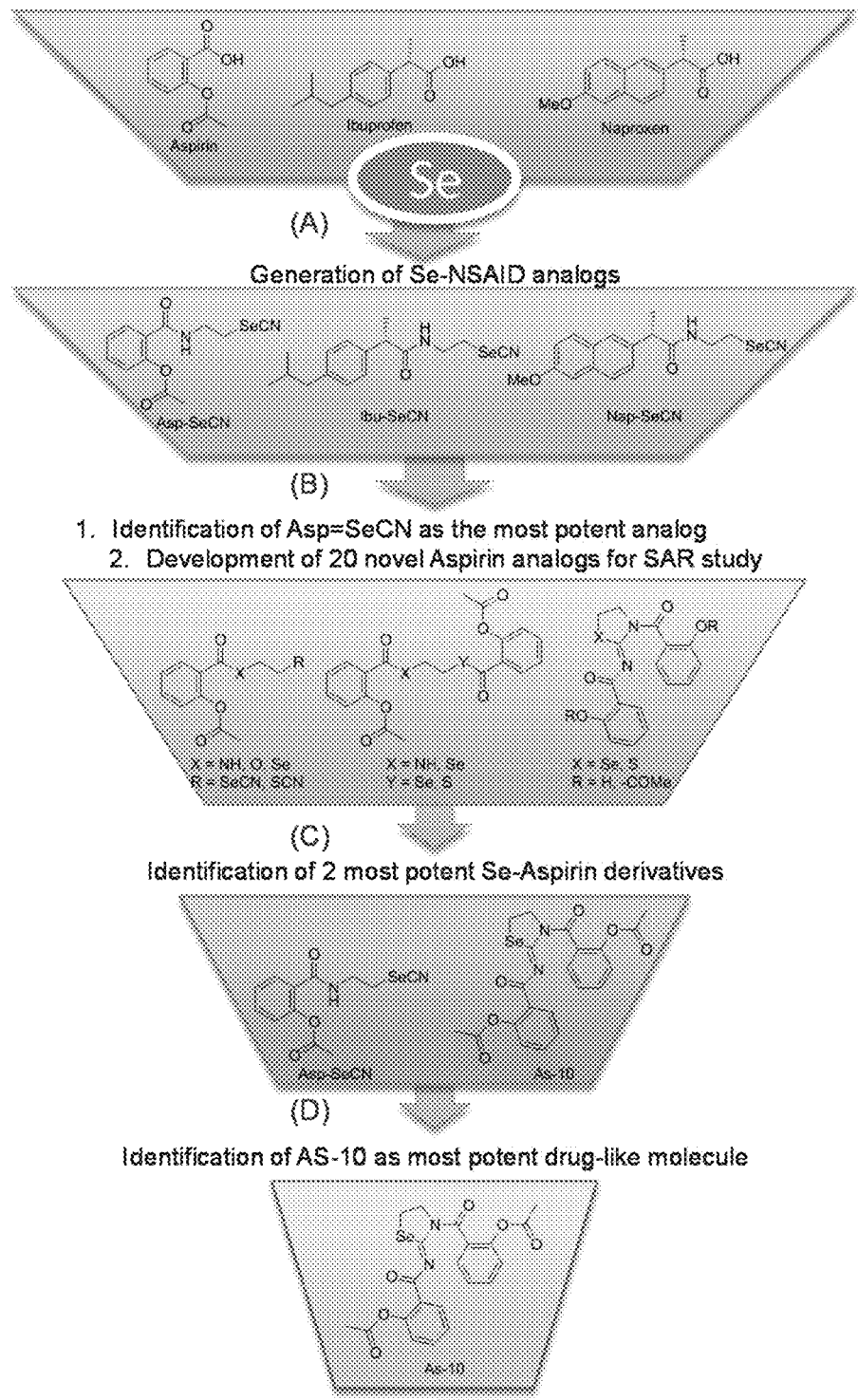
FIG. 1 depicts a flow chart including the SAR study and identification of AS-10 as a significantly potent agent.

This invention includes the unexpected identification of novel selenazolidine and thiazolidine compounds that are useful for the treatment of various diseases and disorders such as cancer. As demonstrated herein, the compounds of the present invention have been shown to be effective chemotherapeutic agents for the treatment of pancreatic cancer.

The compounds of the present invention provide improvements over other cancer therapeutics known in the prior art. In one embodiment, compounds of the invention are more potent than known chemotherapeutic agents such as gemcitabine. In addition, the compounds of the invention are useful as agent that selectively kill cancer cells and eliminate toxicity related to NSAIDs. For example, compound AS-10 was found to reduce PC cell growth more potently than current PC therapy (gemcitabine) and to be selective towards cancer cells.

The compounds of the present invention may also be useful to treat a disease or disorder where modulating the NF-κB pathway may be therapeutically beneficial. In one embodiment, the NF-κB pathway is inhibited. For example, compound AS-10 was found to inhibit translocation of NF-κB from cytoplasm to nucleus in the presence of inflammatory stimuli (TNFα).

The present invention also includes novel methods of treating or preventing cancer using the compounds of the invention. In one embodiment, the cancer is selected from the group consisting of lung cancer, colon cancer, colorectal cancer, melanoma, breast cancer, ovarian cancer, prostate cancer, liver cancer, pancreatic cancer, CNS tumors (including brain tumors), neuroblastoma, leukemia, bone cancer, intestinal cancer, lymphoma, and combinations thereof. In one embodiment, the cancer is pancreatic cancer.

The present invention also includes novel methods of treating or preventing an inflammatory condition using the compounds of the invention. The present invention also includes novel methods of treating or preventing pain using the compounds of the invention. In one embodiment, the present invention includes compositions and methods useful in the treatment and prevention of any disease in a subject in need thereof which may also be treated or prevented by administering an NSAID to the subject. For example, compound AS-10, which contains two aspirinyl moieties flanked to a cyclic selenazolidine ring, was found to be ~350 times more potent than aspirin in inhibiting growth of cancer cells, suggesting that compounds of the invention may be useful for treating inflammation, general fever or pain at a significantly lower dose. In one embodiment, using in compounds of the invention instead of aspirin reduces aspirin related side effects, such as gastrointestinal bleeding.

The present invention includes a composition comprising at least one compound of the invention, wherein the composition optionally further comprises at least one additional therapeutic agent. In one embodiment, the additional therapeutic agent is a chemotherapeutic agent. For example, compound AS-10 was found to significantly potentiate the apoptotic ability of gemcitabine in PC cells

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, at least one sign or symptom of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

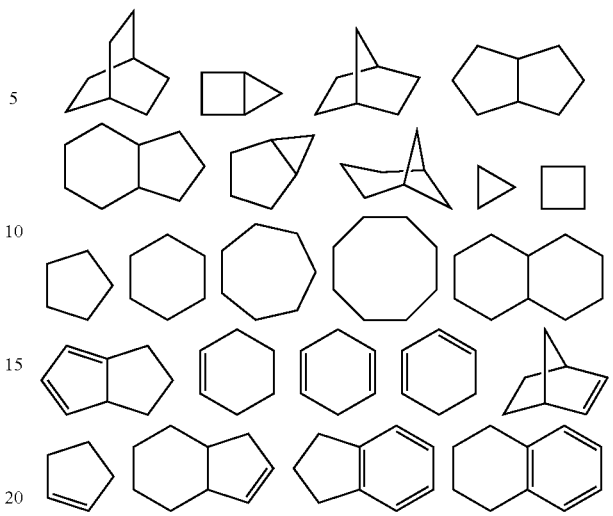

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

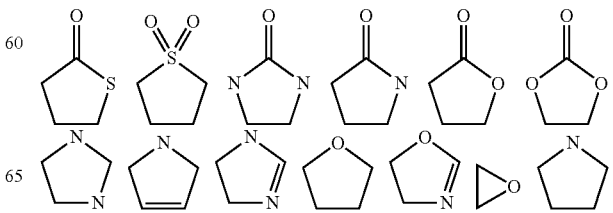

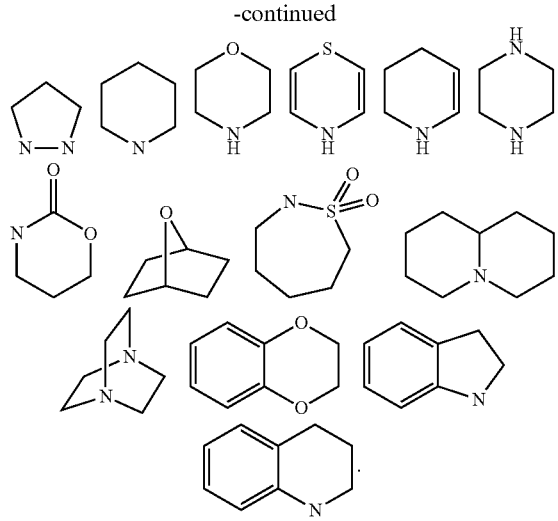

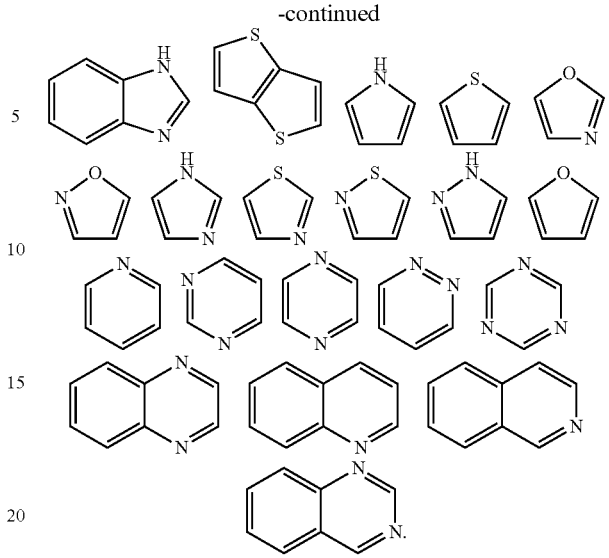

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

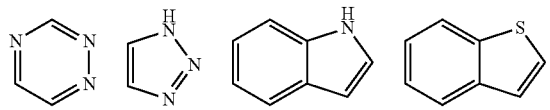

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(═O)$_2$alkyl, —C(═O)NH[substituted or unsubstituted alkyl, or substituted or unsubstituted phenyl], —C(═O)N[H or alkyl]$_2$, —OC(═O)N[substituted or unsubstituted alkyl]$_2$, —NHC(═O)NH [substituted or unsubstituted alkyl, or substituted or unsubstituted phenyl], —NHC(═O)alkyl, —N[substituted or unsubstituted alkyl]C(═O)[substituted or unsubstituted alkyl], —NHC(═O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(═O)$_2$—CH$_3$, —C(═O)NH$_2$, —C(═O)—NHCH$_3$, —NHC(═O)NHCH$_3$, —C(═O)CH$_3$, —ON(O)$_2$, and —C(═O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds Useful within the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt or solvate thereof:

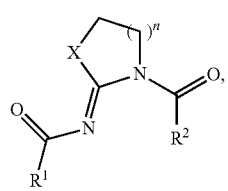

(I)

wherein in formula (I):

R$^1$ and R$^2$ are each independently selected from the group consisting of —C$_1$-C$_6$ alkyl, —C$_1$-C$_6$ fluoroalkyl, —C$_1$-C$_6$ heteroalkyl, —OR$^3$, —SR$^3$, —C(═O)R$^3$, —OC(═O)R$^3$, —OCO$_2$R$^3$, —CH(R$^3$)$_2$, —N(R$^3$)$_2$, —C(OH)(R$^3$)$_2$, —C(NH$_2$)(R$^3$)$_2$, cycloalkyl, aryl, heteroaryl, —C$_1$-C$_6$ alkyl-aryl, —C$_1$-C$_6$ alkyl-heteroaryl, —C$_1$-C$_6$ alkyl-cycloalkyl, wherein the alkyl, cycloalkyl, aryl, heteroaryl, alkylaryl, alkylheteroaryl, and alkylcycloalkyl, group may be optionally substituted;

each occurrence of R$^3$ is independently selected from the group consisting of H and —C$_1$-C$_6$ alkyl;

n is an integer between 1 and 3; and

X is selected from the group consisting of Se and S, a salt or solvate thereof, and any combinations thereof.

In one embodiment, X is Se. In one embodiment, X is S.

In one embodiment, n is 1. In one embodiment, n is 2. In one embodiment, n is 3.

In one embodiment, the compound of the invention is selected from the group consisting of:

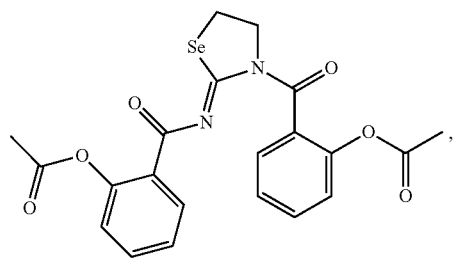 [SMILES: CC(=O)Oc1ccccc1C(=O)/N=C1\[Se]CCN1C(=O)c1ccccc1OC(C)=O]

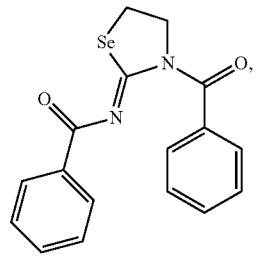

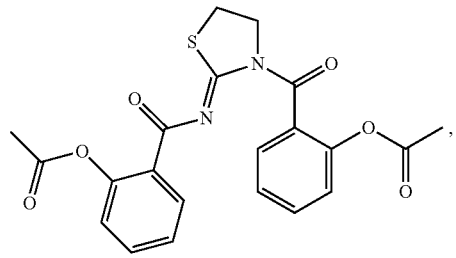 [SMILES: CC(=O)Oc1ccccc1C(=O)/N=C1\[Se]CCN1C(=O)c1ccccc1OC(C)=O]

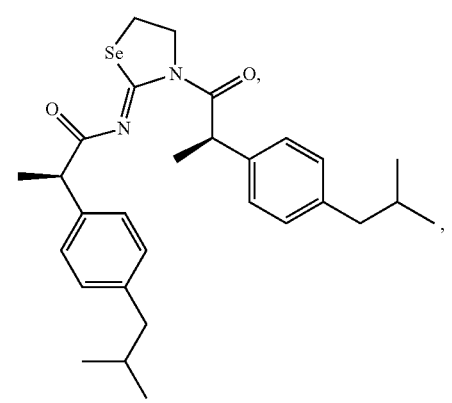

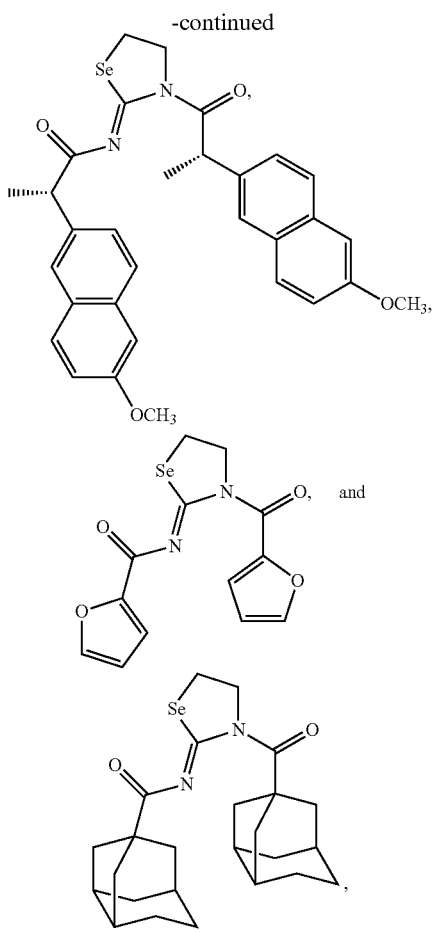

a salt or solvate thereof, and any combinations thereof.
In one embodiment, the compound is:

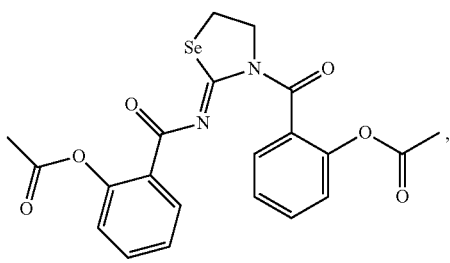 [SMILES: CC(=O)Oc1ccccc1C(=O)/N=C1\[Se]CCN1C(=O)c1ccccc1OC(C)=O]

a salt or solvate thereof, and any combinations thereof.

Preparation of the Compounds of the Invention

Compounds of formula (I) may be prepared by the general schemes described herein, using the synthetic method known by those skilled in the art. The following examples illustrate non-limiting embodiments of the invention.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}F$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

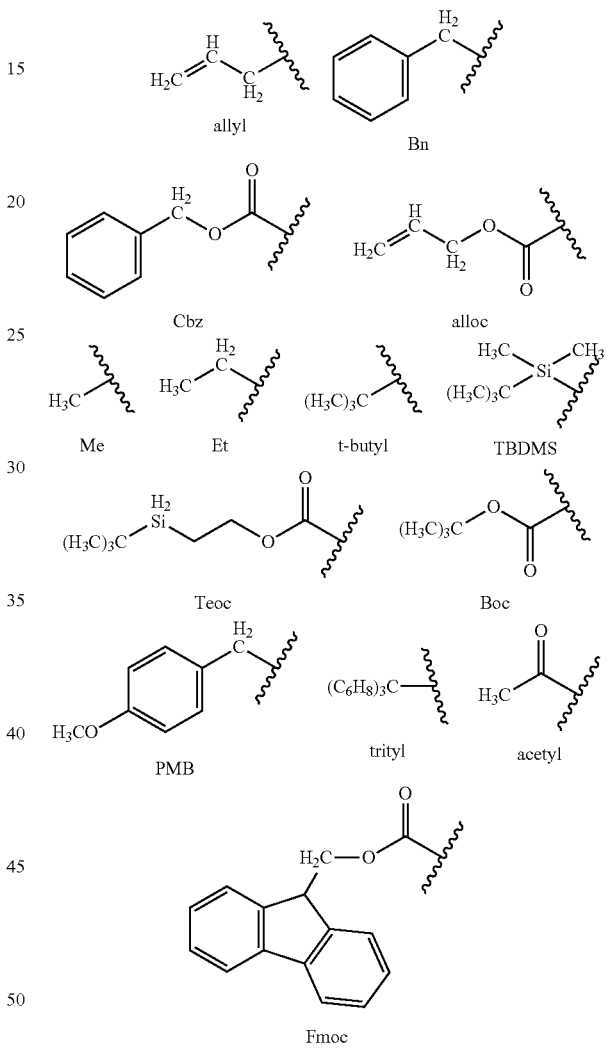

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods of the Invention

The invention includes a method of treating or preventing cancer in a subject in need thereof. The method comprises administering to the subject an effective amount of a therapeutic composition comprising a compound of the invention. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the compositions of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers that can be treated with the compositions of the invention include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, that can be treated with the compositions of the invention, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In one embodiment, the cancer is selected from the group consisting of lung cancer, colon cancer, colorectal cancer, melanoma, breast cancer, ovarian cancer, prostate cancer, liver cancer, pancreatic cancer, CNS tumors (including brain tumors), neuroblastoma, leukemia, bone cancer, intestinal cancer, lymphoma, and combinations thereof. In one embodiment, the cancer is pancreatic cancer. In one embodiment, the cancer is prostate cancer. In one embodiment, the method further comprises administering to the subject an additional therapeutic agent. In one embodiment, the therapeutic agent is gemcitabine.

The invention also includes a method of treating or preventing pain or inflammation in a subject in need thereof. The method comprises administering to the subject an effective amount of a therapeutic composition comprising a compound of the invention. In one embodiment, the inflammation is selected from the group consisting of arthritic disorders, psoriasis, allergies, opioid tolerance, Crohn's Disease, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, and myocardial ischemia. In one embodiment, the arthritic disorder is selected from the group consisting of rheumatoid arthritis, spondyloarthropathies, gouty arthritis, osteoarthritis, systemic lupus erythematosus and juvenile arthritis. In one embodiment, the method further comprises administering to the subject an additional therapeutic agent.

In one embodiment, the pain is selected from the group consisting of pain resulting from cancer, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures. In one embodiment, the method further comprises administering to the subject an additional therapeutic agent.

The invention also includes a method of treating or preventing a disease or disorder associated with the NF-κB pathway in a subject in need thereof. The method comprises administering to the subject an effective amount of a therapeutic composition comprising a compound of the invention. Non-limiting examples of diseases or disorder associated with reactive oxygen species include ischemic diseases, inflammatory diseases, autoimmune diseases, cancer metastasis and invasion, and cachexia.

The invention also includes a method of treating or preventing a disease or disorder associated with reactive oxygen species (ROS) in a subject in need thereof. The method comprises administering to the subject an effective amount of a therapeutic composition comprising a compound of the invention. Non-limiting examples of diseases or disorder associated with reactive oxygen species include arteriosclerosis, myocardial infarction, diabetes, and cancer.

In one embodiment, administering the compound of the invention to the subject allows for administering a lower dose of the therapeutic agent compared to the dose of the therapeutic agent alone that is required to achieve similar results in treating or preventing cancer in the subject. For example, in one embodiment, the compound of the invention enhances the anti-cancer activity of the additional therapeutic compound, thereby allowing for a lower dose of the therapeutic compound to provide the same effect. In another embodiment, administering the compound of the invention to the subject allows for administering a lower dose of the therapeutic agent compared to the dose of the therapeutic agent alone that is required to achieve similar results in treating or preventing pain or inflammation in the subject.

In one embodiment, the compound of the invention and the therapeutic agent are co-administered to the subject. In another embodiment, the compound of the invention and the therapeutic agent are co-formulated and co-administered to the subject.

In one embodiment, the subject is a mammal. In another embodiment, the mammal is a human.

Combination Therapies

The compounds of the present invention are intended to be useful in combination with one or more additional compounds. In certain embodiments, these additional compounds may comprise compounds of the present invention or therapeutic agents known to treat or reduce the symptoms or effects of cancer. Such compounds include, but are not limited to, chemotherapeutics and the like. In other embodiments, these additional compounds may comprise therapeutic agents known to treat or reduce the symptoms or effects of pain or inflammation.

In non-limiting examples, the compounds of the invention may be used in combination with one or more therapeutic agents (or a salt, solvate or prodrug thereof).

In certain embodiments, the compound of the invention may be administered to a subject in conjunction with (e.g. before, simultaneously, or following) any number of relevant treatment modalities including chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the compounds of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compounds of the present invention are administered following B-cell ablative therapy such as agents that react with CD20, e.g., Rituxan. In another embodiment, the compounds of the present invention are administered in conjunction with Ospemifene, Tamoxifen, Raloxifene, or other drugs such as ICI 182,780 and RU 58668. Tamoxifen and Raloxifene may act as partial antiestrogens, and the drugs such as ICI 182,780 and RU 58668 may act as full antiestrogens. In another embodiment, the compounds of the invention are administered in conjunction with aromatase inhibitors. Non-limiting examples of aromatase inhibitors include Exemestane, Letrozole, and Anastrozole. In one embodiment, the therapeutic agent is gemcitabine.

In certain embodiments, the compounds of the invention may be administered to a subject in conjunction with (e.g. before, simultaneously, or following) an anti-inflammatory agent selected from the group consisting of nonsteroidal agents ("NSAIDS") such as salicylates (e.g., salsalate, mesalamine, diflunisal, choline magnesium trisalicylate), diclofenac, diflunisal, etodolac, fenoprofen, flurbiprofen, ibuprofen, indomethacin, mefenamic acid, nabumetone, naproxen, piroxicam, phenyl butazone, ketoprofen, S-ketoprofen, ketorolac tromethamine, sulindac, tolmetin). Other anti-inflammatory drugs include steroidal agents such as beclomethasone, betamethasone, cortisone, dexamethasone, fluocinolone, flunisolide, fluticasone proprionate, fluorinated-corticoids, triamcinolone-diacetate, hydorcortisone, prednisolone, methylprednisolone, and prednisone. Immunosuppressive agents (e.g., adenocorticosteroids, cyclosporin), antihistamines and decongestants (e.g., astemizole(histamine I II-receptor antagonist), azatidine, brompheniramine, clemastine, chlorpheniramine, cromolyn, cyproheptadine, diphenylimidazole, diphenhydramine hydrochloride, hydroxyzine, glycyrrhetic acid, homochlorocyclizine hydrochloride, ketotifen, loratadine, naphazoline, phenindamine, pheniramine, promethazine, terfenadine, trimeprazine, tripelennamine, tranilast, and the decongestants phenylpropanolamine and pseudoephedrine. In one embodiment, the therapeutic agent is a nonsteroidal anti-inflammatory drug (NSAID), as would be understood by one of ordinary skill in the art.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either before or after the onset of cancer. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the cancer in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Discovery of Selena-Thia-Zolidines and Identification of AS-10

The results describe herein demonstrate that a novel small molecule, AS-10, was lethal to pancreatic cancer (PC) cells. The mechanism of action of AS-10 responsible for inhibiting the growth of PC cells was investigated. In vitro, AS-10 reduced PC cell growth with an EC50, in the range of 2.5 to 5 µM. Growth arrest was confirmed by cell cycle studies, which showed that AS-10 induced G1 and G2 cell cycle arrest. The cell cycle arrest was associated with an increase of cell cycle inhibitory markers like p21 and p27. The effect of AS-10 on cell cycle was translated into activation of p50, confirmed by caspase 3/7 activity, PARP cleavage and Annexin V staining. Due to its structural characteristics, the effect of AS-10 on the inflammatory NF-κB pathway was evaluated. The results demonstrated that in Panc-1 cells, AS-10 inhibited NF-κB DNA binding activity as well as NF-κB translocation to the nuclei in the presence of inflammatory stimuli (tumor necrosis factor (TNFα)).

Although not wishing to be bound by any particular theory, the data described herein suggests that the anticancer activity of AS-10 may, at least partially, be due to induction of ROS, since ROS quencher (NAC) was able to inhibit partially the activity of AS-10. Further, AS-10 was found to be more potent than aspirin; hence low doses of AS-10 may be useful to reduce the GI toxicity that aspirin causes.

The activity of AS-10 in combination with gemcitabine was also examined, and the results showed that AS-10 synergistically potentiated gemcitabine activity in PC cells. The results described herein demonstrate that AS-10 may be useful as a therapeutic agent for PC.

The materials and methods employed in these experiments are now described.

Synthesis of Selena-/Thia-Zolidine Compounds

Figure 2:
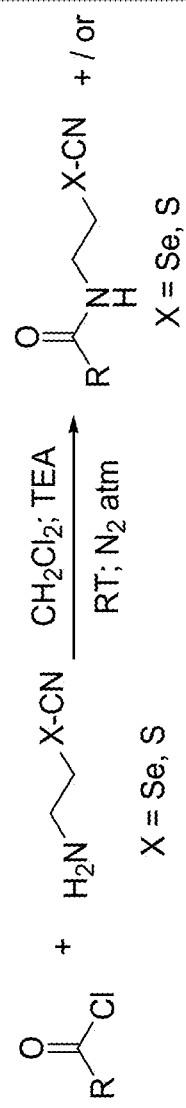
FIG. 2 is a scheme of an exemplary synthesis of —SeCN and Se-heterocyclic compounds.

The cyclic selena-/thia-zolidines were synthesized as outlined in FIG. 2. Depending on the acyl chloride used, a novel class of Se/S-heterocycles were obtained. Table 1 includes the representative reactions with the types of compounds and their ratio obtained with various acyl chlorides.

TABLE 1

Representative reactions and ratios for open chain and cyclic Se derivatives (selenazolidines) obtained for each reaction.

| R | SeCN | Se-cycle |
|---|---|---|
| (4-isobutylphenyl)ethyl | 100% | — |
| (6-methoxynaphthalen-2-yl)ethyl | 100% | — |
| 2-acetoxyphenyl | — | 100% |
| phenyl | — | 100% |
| furan-2-yl | 21% | 79% |

TABLE 1-continued

Representative reactions and ratios for open chain and cyclic Se derivatives (selenazolidines) obtained for each reaction.

| R | SeCN | Se-cycle |
|---|---|---|
| adamantyl | 70% | 30% |

2-((3-(2-acetoxybenzoyl)-1,3-selenazolidin-2-ylidene)carbamoyl)phenyl acetate (AS-10). Overall yield 49%. $^1$H NMR (500 MHz, CDCl$_3$) δ 2.28 (s, 3H, CH$_3$); 2.40 (s, 3H, CH$_3$); 3.12 (t, 2H, CH$_2$—Se); 4.38 (t, 2H, CH$_2$—NH); 6.72 (dd, 1H); 6.91 (td, 1H); 7.00 (dd, 1H); 7.21 (dd, 1H); 7.40 (td, 1H); 7.44 (td, 1H); 7.55 (td, 1H); 7.65 (dd, 1H). $^{13}$C NMR (150 MHz, CDCl$_3$) δ 19.7 (CH$_2$), 20.8 (CH$_3$), 21.2 (CH$_3$), 49.8 (CH$_2$), 122.9, 123.4, 125.1, 126.0, 127.0, 129.7, 129.8, 131.5, 132.7, 133.8, 147.4, 151.3 (aryl), 166.8, 168.6, 169.9, 171.8, 173.6 (C=O). HRMS (ESI) calcd for C$_{21}$H$_{19}$N$_2$O$_6$Se [M+H]$^+$: 475.0403. Found: 475.0404.

ASD-171

Figure 4:
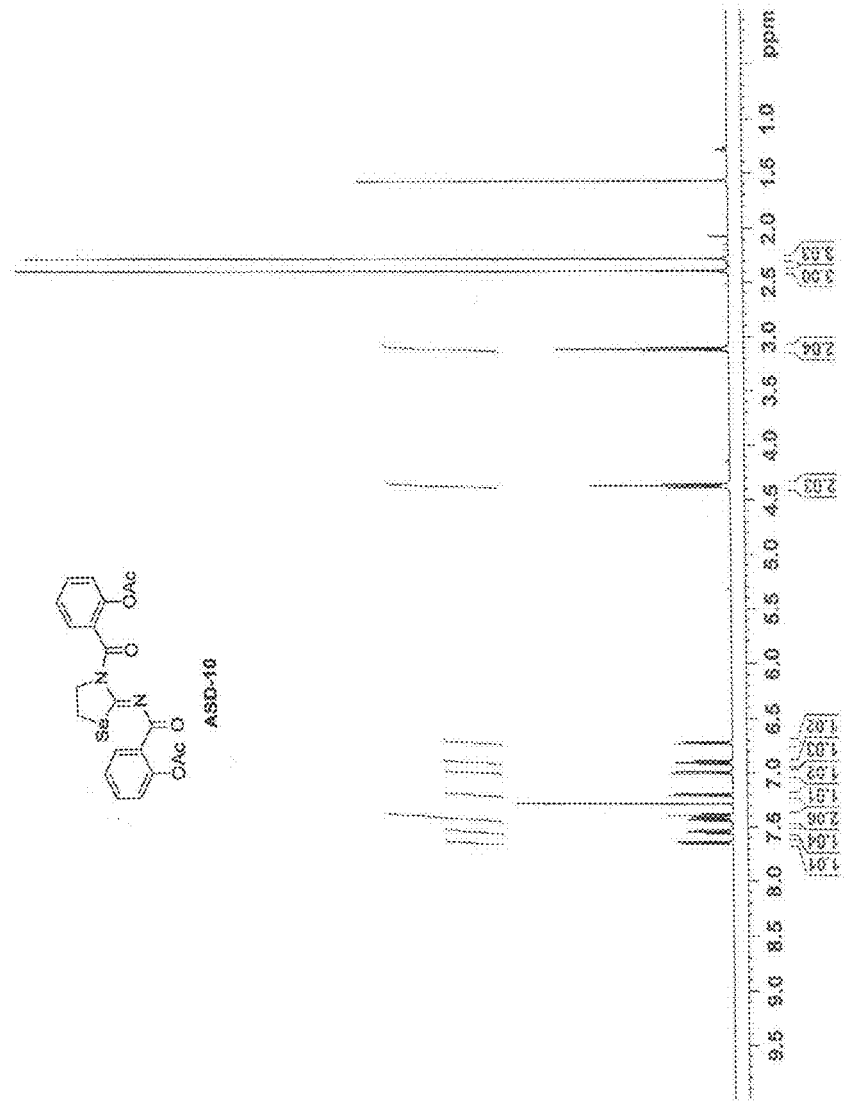
FIG. 4 is a $^1$H-NMR spectrum of ASD-171.

N-(3-benzoyl-1,3-selenazolidin-2-ylidene)benzamide (ASD-171). Overall yield 63%. $^1$H NMR (500 MHz, CDCl$_3$) δ 3.20 (t, 2H, CH$_2$—Se); 4.37 (t, 2H, CH$_2$—NH); 7.19 (t, 2H); 7.36 (dd, 2H); 7.40 (td, 1H); 7.47 (t, 2H); 7.56 (td, 1H); 7.72 (td, 2H). (FIG. 4 includes the $^1$H-NMR spectrum of ASD-171)

ASD-123

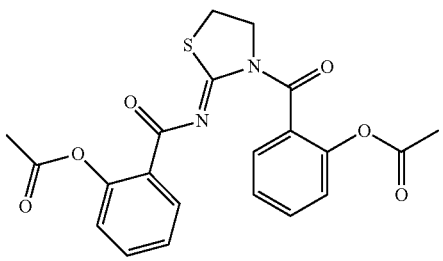 [SMILES: CC(=O)Oc1ccccc1C(=O)/N=C1\SCCN1C(=O)c1ccccc1OC(C)=O]

2-((3-(2-acetoxybenzoyl)-1,3-thiazolidin-2-ylidene)carbamoyl)phenyl acetate (ASD-123). $^1$H NMR (500 MHz, CDCl$_3$) δ 2.28 (s, 3H, CH$_3$); 2.39 (s, 3H, CH$_3$); 3.25 (t, 2H, CH$_2$—S); 4.27 (t, 2H, CH$_2$—NH); 6.69 (dd, 1H); 6.89 (td, 1H); 6.99 (dd, 1H); 7.23 (d, 1H); 7.38 (td, 1H); 7.42 (td, 1H); 7.55 (td, 1H); 7.63 (dd, 1H).

X-Ray Crystallography

A colorless pyramid shaped crystal of AS-10 (C$_{21}$H$_{18}$N$_2$O$_6$Se) with approximate dimensions 0.10×0.13×0.16 mm, was used for the X-ray crystallographic analysis. The X-ray intensity data were measured at 298(2) K, on a Bruker SMART APEX CCD area detector system equipped with a graphite monochromator and a MoKα fine-focus sealed tube (λ=0.71073 Å) operated at 1600 watts power (50 kV, 32 mA). The detector was placed at a distance of 5.8 cm from the crystal.

A total of 1850 frames were collected with a scan width of 0.3° in ω and an exposure time of 10 seconds/frame. The total data collection time was about 9 hours. The frames were integrated with the Bruker SAINT software package using a narrow-frame integration algorithm. The integration of the data using a Monoclinic unit cell yielded a total of 21157 reflections to a maximum θ angle of 28.81° (0.90 Å resolution), of which 5091 were independent, completeness=96.2%, $R_{int}$=0.0426, $R_{sig}$=0.0413 and 3345 were greater than 2σ (I). The final cell constants: a=10.2512(12) Å, b=9.0119(11) Å, c=21.927(3) Å, α=90°, β=92.469(2)°, γ=90°, volume=2023.8(4) Å$^3$, are based upon the refinement of the XYZ-centroids of 3172 reflections above 20σ(I) with 2.581°<θ<23.631°. Analysis of the data showed negligible decay during data collection. Data were corrected for absorption effects using the multiscan technique (SADABS). The ratio of minimum to maximum apparent transmission was 0.6073.

The structure was solved and refined using the Bruker SHELXTL (Version 6.1) Software Package, using the space group P2(1)/n, with Z=4 for the formula unit, C$_{21}$H$_{18}$N$_2$O$_6$Se. Hydrogen atoms were placed geometrically. The final anisotropic full-matrix least-squares refinement on F$^2$ with 273 variables converged at R1=4.39%, for the observed data and wR2=11.25% for all data. The goodness-of-fit was 1.017. The largest peak on the final difference map was 0.470 e$^-$/Å$^3$ and the largest hole was −0.449 e$^-$/Å$^3$. Based on the final model, the calculated density of the crystal is 1.554 g/cm$^3$ and F(000) amounts to 960 electrons.

Figure 3:
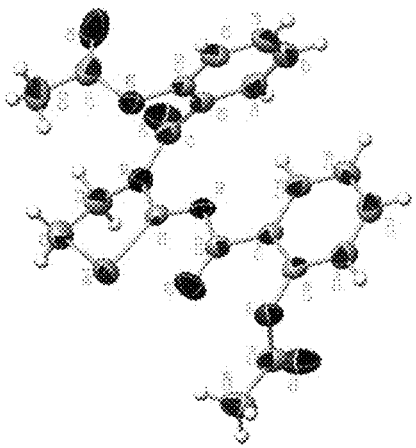
FIG. 3 is an image of the Crystal structure of AS-10.

Taking into account the entire structural data obtained, the structure of AS-10 was determined is shown in FIG. 3.

Reagents

AS-10 stock was dissolved in DMSO at 10 mM concentration and store at −20° C. New stocks were made every 7 days in DMSO. Antibodies were ordered from following companies: Cell signaling (cyclin B1 (4138s), caspase 3 (9662s), caspase 9 (9508s), IκBα (9242s), Bcl-xL (2762s), Mcl-1 (5453s) and PARP (9542s)), Abcam (PCNA (ab18197), p100/p50 (ab31412), GAPDH (51'74p) and p65 (ab7970)), Santa Cruz Biotechnology (p21 (sc-397) and p27 (sc-528)), Jackson Immuno Research (Alexa fluor 680 (711-625-152) and Donkey serum (017-000-002)) and Sigma-Aldrich (β-actin (a-5441) and Tubulin-β (c-4585)). Rabbit IgG-chip grade protein was ordered from abcam (ab37415), Propidium Iodide (P4170-10MG), Ribonuclease A (RNAse A, R6513-10MG) and Crystal Violet (C6158-50G) from Sigma.

Cell Culture

Panc-1, BxPC3, MEFs, MDA-MB-231 and 1205Lu cells were maintained in DMEM medium; DU145, NCI-H460Z and UACC903 cells were maintained in RPMI 1640 medium; SKOV3, HT29, HCT116 and RKO cells were maintained in McCoy's 5A medium; HEPG2 cells were maintained in Eagle's Minimum Essential Medium (EMEM) supplemented with 10% fetal bovine serum (FBS) and 100 units/mL of penicillin and streptomycin at 37° C. and 5% CO$_2$. All cell lines were obtained from ATCC.

Cell Viability Assay

MTT (3-(4,5-dimethylthiazol-2-yl)-2,5-diphenyltetrazolium) assay was performed to determine the effect of AS-10 on cancer cell viability (Plano et al., 2016, J. Med. Chem. 1946-1959; Alcolea et al., 2012, Eur. J. Med. Chem. 113: 134-144; Kumar et al., 2014, Eur. J. Med. Chem. 81:267-276). Briefly, 3×10$^3$ cells were treated with different concentrations of AS-10 in triplicate in a 96-well plate for different time points. MTT solution (20 μL of 5.0 mg/mL solution) was added to each well, three hours prior to termination time point and incubated at 37° C. Resultant formazan crystals, at termination time point, were dissolved in 50 μL DMSO. The plate was subjected to a 96-well multiscanner (Dynex Technologies, MRX Revelation; Chantilly, Va., USA) for measuring the optical densities at 570 nm and 630 nm. IC$_{50}$ values were determined by performing non-linear regression using Graphpad Prism software.

Colony Formation Assay

Crystal violet staining method was utilized for performing colony formation assay (Franken et al., 2006, Nat. protoc. 1:2315-2319). In brief, Panc-1 cells were treated with vehicle control (DMSO). 2.5 μM or 10 μM of AS-10 for 48 h. After 48 h treatment period, cells were trypsinized and live cells were counted using tryphan blue dye exclusion assay. Tissue culture plates of size 60×15 mm were seeded with 100 live cells from vehicle treated and 5000 live cells from AS-10 treated cells. Cells were allowed to form colonies for 17 days in DMEM free from DMSO or AS-10 at 37° C. in a 5% CO$_2$ chamber. After 17 days' colonies were stained with 0.5% alcoholic crystal violet. Percentage Plating efficiency (PE) was calculated by the formula: % PE=number of colonies*100/number of cells plated. Data plotted as % relative PE.

Cell Cycle Analysis

Flow cytometry was used to determine the cell cycle phases (Plano et al., 2016, J. Med. Chem. 1946-1959). In brief, Panc-1 cells were serum starved for 72 h, followed by treatment with different doses of AS-10 in 10% serum containing media for different time points. Treated cells were fixed in 70% cold ethanol at the end of each time point. Cells were fixed for a minimum of 4 h at 4° C. Following fixation, cells were washed with 1×PBS and were re-suspended in Propidium iodide (PI) staining solution (0.1% (v/v) triton X-100, 20 mg DNAse-free RNAse A and 2 mg of PI in 100 mL PBS). Cells were incubated in the staining solution for 15 minutes at room temperature and then analyzed by a BD FACS Calibur (BD Biosciences) for total DNA content. Modfit software (BD Biosciences) was used to obtain the histograms.

Western Blot Analysis

Whole-cell lysates were made by subjecting AS-10 treated Panc-1 cells to RIPA lysis buffer (Thermo Scientific, USA) containing protease (Roche, USA) and phosphatase inhibitor cocktails (Sigma-Aldrich, USA) (Plano et al., 2016, J. Med. Chem. 1946-1959). Lysates were spun at 15,000 rpm for 10 minutes. Resulting supernatant was stored at −80° C. until use. NuPAGE gel 4-12% (Life Technologies, Carlsbad, Calif.) was used to resolve the lysates, followed by electro-transfer to PVDF membrane. After the transfer membrane was blocked with 5% non-fat milk and probed with different antibodies. Protein of interest were detected by using enhanced Chemiluminescent reagent (Life technologies, USA). Blots were stripped using Restore Western blot stripping buffer (Thermo Scientific, USA) to save time and samples.

Annexin V Assay

Muse Annexin V & Dead Cell kit was used to determine the apoptosis cells in AS-10 treated Panc-1 cells (Plano et al., 2016, J. Med. Chem. 1946-1959). The Muse Annexin V & Dead cell assay contains Annexin V to detect phosphatidylserine (PS) on the outer surface of cells. The kit also contains a dead cell marker, 7-amino-actinomycin D (7-AAD). 7-AAD molecule does not enter live or early apoptotic cells which have not lost their cell membrane integrity (Millipore, MCH100105). In brief, Panc-1 ($1.5 \times 10^5$) cells were treated with a given dose of AS-10 or DMSO for appropriate time (0, 6, 12, 24, 36, or 48 h). Both floating cells as well as adherent cells were collected and subjected for Annexin V staining using Muse Annexin V & Dead Cell kit with Muse cell analyzer (EMD Millipore, Billerica, Mass., USA). The obtained data were analyzed using Muse 1.4 software.

Caspase 3/7 Activity Assay

To evaluate the efficacy of AS-10 in inducing caspase 3, Panc-1 cells were treated with AS-10 at different concentrations for different time points. Caspase 3/7 activity was measured using Muse Caspase-3/7 Assay kit with Muse cell analyzer (EMD Millipore, Billercia, Mass. USA) according to manufacturer's protocol (Plano et al., 2016, J. Med. Chem. 1946-1959). In brief, the Muse Caspase 3/7 kit contains a reagent namely NucView for detection of activated caspase 3/7. The reagent is cell membrane permeable and contains a DNA binding dye that is linked to a DEVD peptide substrate. In presence of activated caspase 3/7, DEVD is cleaved and DNA binding dye is released. Therefore, cells with active caspase 3/7 activity will yield high fluorescence. (Ref Millipore, Catlog No. MCH100108). The kit also contains a dead cell marker, 7-AAD, for detection of cells with compromised cell membrane. Data from Muse cell analyzer were analyzed using Muse 1.4 software.

Electrophoretic Mobility Shift Assay (EMSA)

To determine NF-κB activation, Panc-1 ($1 \times 10^6$) cells were treated with different doses of AS-10 for 6 h. Thirty minutes before termination cells were stimulated with 100 ng/mL TNF-α (which is about 3.9 nM in media after addition). At the end of thirty minutes, cells were immediately stored on ice. Nuclear and cytosolic extracts were prepared as described previously (Pandey et al., 2007, J. Biol. Chem. 282: 17340-17350). Nuclear lysates were subjected to EMSA following the protocol (Pandey et al., 2007, J. Biol. Chem. 282: 17340-17350). The dried gels were exposed to X-ray films at −80° C. for exposure.

Immunocytochemistry for NF-κB p65 Localization

Immunocytochemistry was used to determine the translocation of p65 from cytoplasm to nucleus in presence of inflammatory stimuli either with vehicle or AS-10 (10 μM). In a 12 well plate, Panc-1 cells ($1.6 \times 10^5$) were seeded on top of a small cover slip in DMEM medium. Cells were allowed to attach to the cover slip overnight at 37° C. incubator with 5% $CO_2$. The next day, cells were treated with 10 μM AS-10 for 6 h and further stimulated with TNF-α (100 ng/mL, 3.9 nM) for 30 min. Exactly after 30 min plates were kept on ice and cells were fixed with 4% Formaldehyde Solution made in PBS for 15 min. Cells were washes three times with 1×PBS, followed by 1 h incubation in blocking medium (0.3% Triton X-100, 5% donkey serum, made in 1×PBS) at room temperature in dark. After blocking coverslips were incubated with primary antibody solution (primary antibody diluted 1:500 in 1% BSA solution containing 0.3% Triton X-100) over night at 4° C. Next day, primary antibody was removed and cover slips were washed three times with 1×PBS. Following incubation with 0.03% $H_2O_2$ for 15 minutes at room temperature in dark. After the incubation, secondary antibody (Alexa fluor 680) was added at dilution of 1:500 in 1% BSA containing 0.3% triton X-100 and further incubated for 1 hr. After incubation, coverslips were washed and mounted on glass slides with mounting medium containing DAPI (17985-50, Electron Microscopy Sciences). Slides were allowed to dry for 2 days and pictures were taken using the DELTA VISION microscope at 60×. Imaris 8.2 software was used for image processing.

Live/Dead Assay

To determine the dead cell population, we used LIVE/DEAD Viability/Cytotoxicity Kit (L3224, Life technologies, USA). Panc-1 cells were treated with either DMSO, gemcitabine (50 μM), or AS-10 (2.5 μM) or in combination for 48 h. Live and dead cells were determined by subjecting treated cells to LIVE/DEAD Viability/Cytotoxicity Kit (Plano et al., 2016, J. Med. Chem. 1946-1959). Calcein-AM can freely travel through the plasma meberane of cells and fluorescents green in presence of intracellular esterase activity, hence green fluorescence indicates live cells. While ethidium homodimer-1 can only enter cells who have lost their plasma membrane integrity or dead cells and fluorescents red. Stained cells were visualized using a fluorescence microscope (Zeiss—Axio Scope.A1) with a 20× objective lens. Percentage values of live and dead cells were calculated.

ROS Measurement

Measurement of total ROS levels in AS-10 treated Panc-1 cells, was performed by using Muse Oxidative Stress Kit (EMD Millipore, Billerica, Mass., MCH10011) as per the manufacturer's protocol. ROS inside the cells are detected by Muse Oxidative Stress Reagent provided in the kit. Two different cell populations of ROS (−) and ROS (+) are identified using the kit. The ROS (−) population is characterized by the M1 peak, while the ROS (+) cells is characterized by M2 peak in the graph. Panc-1 cells treated with H2O2 (0.9 M) were used as the positive control for the classification of M1 and M2 peaks. Percentages of ROS (−) and ROS (+) cells were measured using Muse cell analyzer.

The results of the experiments are now described.

Three different NSAIDs (aspirin, ibuprofen and naproxen) were selected for Se incorporation in order to identify the NSAID that formed the most effective hybrid molecule with Se. 2-selenocyanoethanamine was used as an appropriate Se moiety to introduce in aspirin, ibuprofen and naproxen scaffolds. The in vitro cytotoxic results indicated that only in the case of aspirin the $IC_{50}$ value of the resulting hybrid derivative was significantly lowered (~350 times)

compared with the parent aspirin scaffold. Accordingly, the aspirin was selected to further structural modifications, both with and without Se incorporation.

Several structural modulations were then performed with aspirin scaffold: i) the functional group used to link the aspirin with the Se atom was modulated at the amide, ester and selenoester positions, ii) the functional groups bearing the Se atom were selected among selenocyanate (—SeCN), methylseleno (—SeCH$_3$) and selenide (—Se-aspirin), and (iii) selenazole flanked with aspirinyl moieties.

Taking into account the IC$_{50}$ values obtained for these aspirin analogs in pancreatic cancer cells, Asp-SeCN and AS-10 emerged as potent and promising compounds. S isosteres of these compounds were much less effective.

Even though Asp-SeCN (IC$_{50}$ 1.0-2.5 uM) and AS-10 (IC$_{50}$ 0.5-2.5 uM) were equally cytotoxic to pancreatic cancer cells, AS-10 was significantly less toxic to normal (Mouse Embryonic Fibrolasts) cells (IC$_{50}$>50 uM). This result was also observed in in vivo studies. Here, in Maximum Tolerated Dose (MTD) studies in nude mice, AS-10 (MTD~80 mg/kg, three times/wk) was ~5 times more tolerable than Asp-SeCN (MTD~16 mg/kg, three times/wk). AS-10, thus emerged as a potent drug-like small molecule with an improved therapeutic index.

Screening of Six Selena-/Thia-Zolidine Analogs

Figure 5:
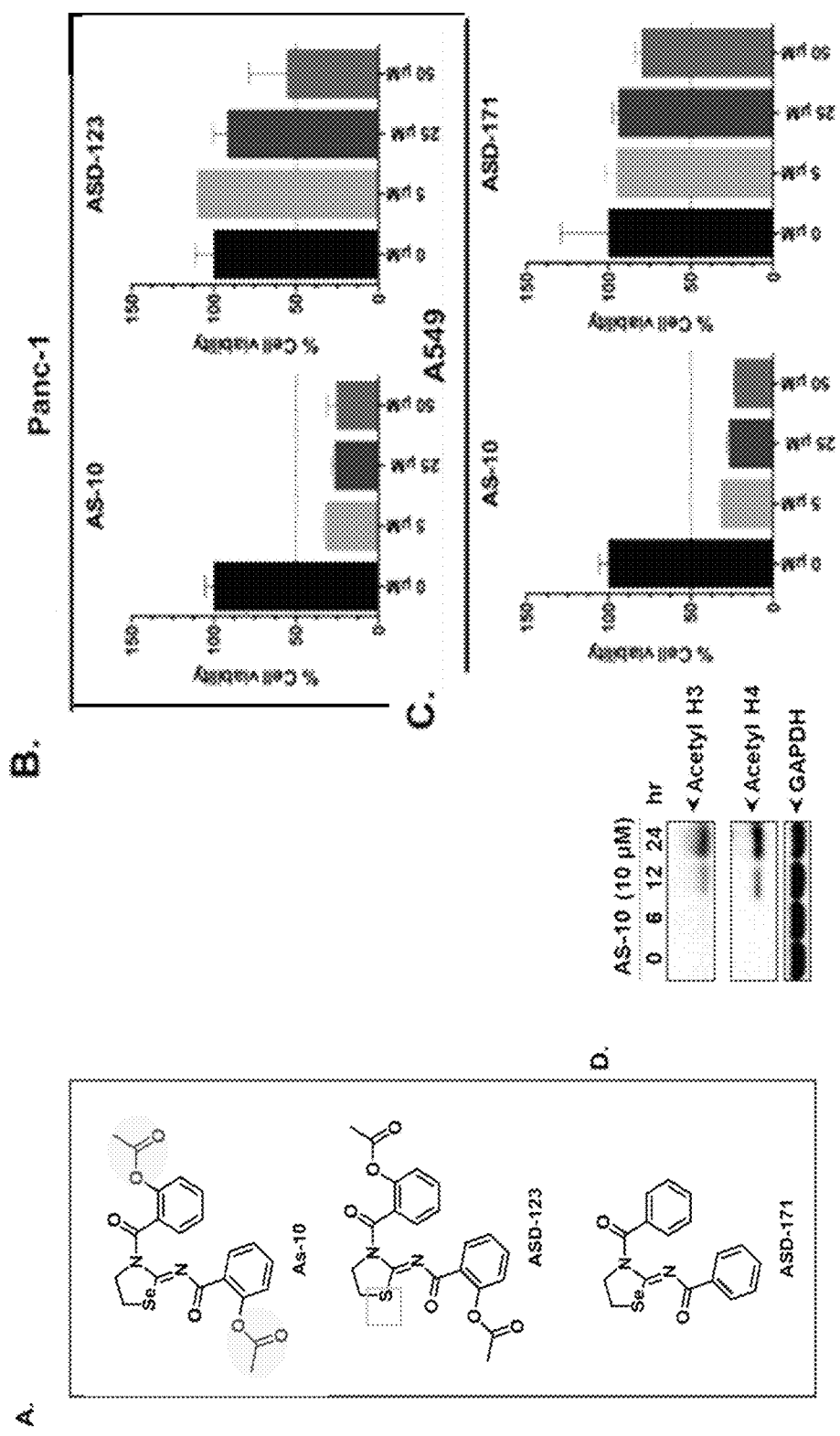
FIG. 5, comprising

Using a MTT assay in different cancer cell lines, AS-10 was found to be the most promising compound when compared to other compounds (FIG. 5). Removal of the acetate functionality of AS-10 (as in ASD-171; FIGS. 5A and 5C) or replacing Se in AS-10 by S (ASD-123; FIGS. 5A and 5B) led to significant loss in the potency of compounds (FIG. 5). Although not wishing to be bound by any particular theory, these results suggest that the acetate functionality and Se are required for potency of the AS-10. Further, Western blot studies with AS-10 in PC cells show that AS-10 is able to acetylate histones (H3 and H4, FIG. 5D).

Effect of AS-10 in Pancreatic Cancer

Figure 6:
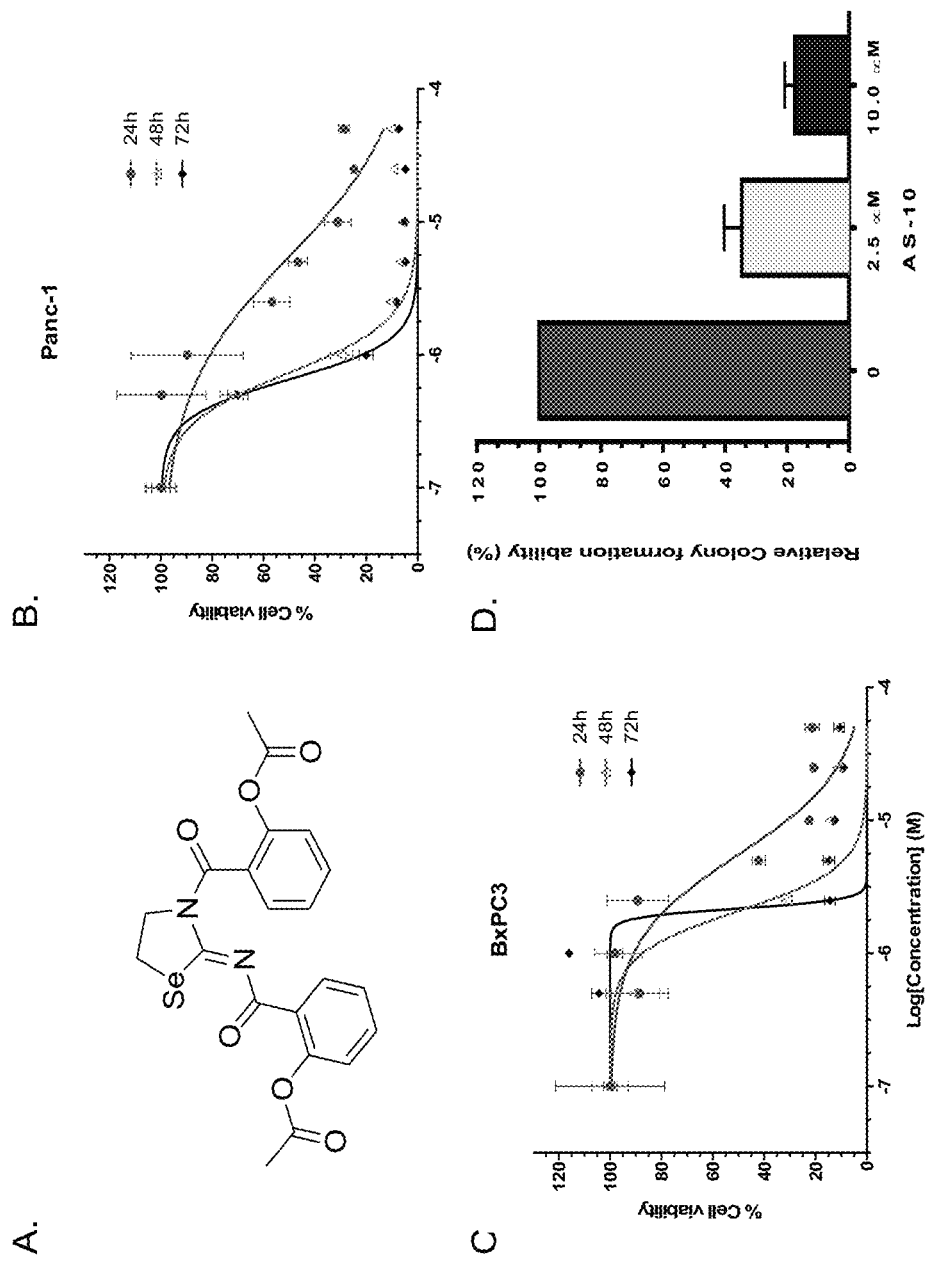
FIG. 6, comprising

To test the anti-cancer activity of AS-10 in pancreatic cancer (PC) cell lines, a MTT assay was performed. PC cell lines, Panc-1 and BxPC3, were treated with AS-10 at different doses at different time points (24, 48, and 72 h). Resulting cells were subjected to MTT cell viability assay. As shown in FIGS. 6B and 6C, AS-10 reduced the cell viability of both the cell lines, with an IC$_{50}$ in the range of 1-5 µM at different time points. Panc-1 cell line was more sensitive to AS-10 and hence further studies were performed on this cell line. The ability of AS-10 on colony formation ability of Panc-1 was examined cells, to further prove its effect on PC cell growth using a different assay. Panc-1 cells were treated with different doses of AS-10 for 48 h. After 48 h, live cells were counted and plated in a new petri dish. Cells were allowed to form colonies for 17 days. At the end of 17 days the colonies were counted and compared to the untreated cells. As shown in FIG. 6D, AS-10 effectively decreased the amount of colonies formed, compared to vehicle treated cells, indicating that the live cells remaining after 48 h of treatment have lost their proliferative ability compared to untreated cells. Although not wishing to be bound by any particular theory, both the results of the MTT assay data and data from colony formation assay suggest that AS-10 potently inhibits PC cells growth in vitro.

Figure 7:
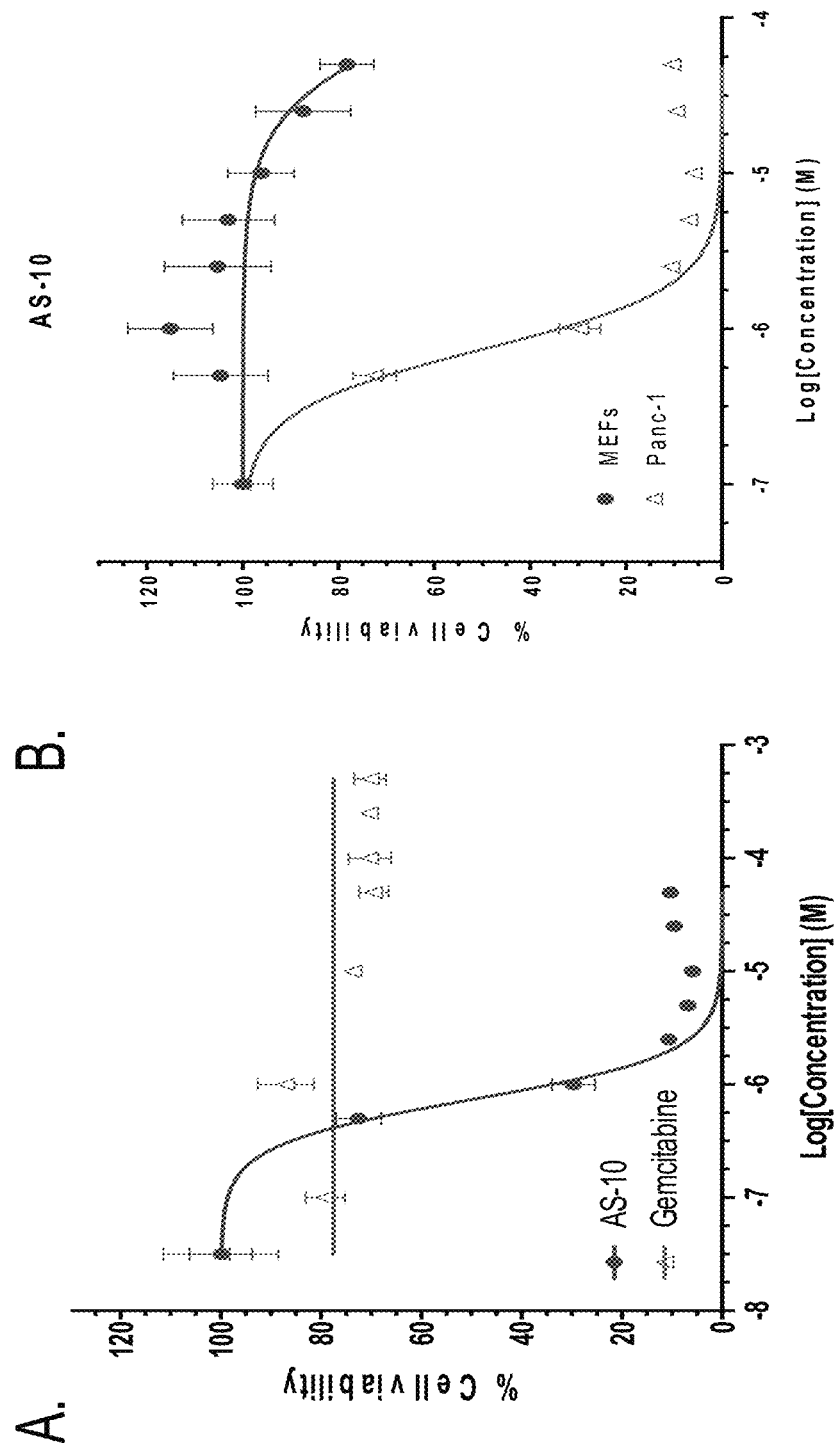
FIG. 7, comprising

AS-10 is More Potent than the Current Standard of Care for PC and More Selective Towards Cancer Cells The potency of AS-10 was compared with gemcitabine, the first line of therapy for PC, using MTT assay. Cells were exposed to AS-10 and gemcitabine at different doses for 48 h and resulting cells were subjected to MTT assay. As shown in FIG. 7A, Panc-1 cells were resistant to gemcitabine treatment even at the highest tested dose of 500 µM for 48 h. In contrast, AS-10 was very potent and exhibited an IC$_{50}$ in the range of 1-2.5 µM at 48 h. Hence, AS-10 proved to be >500 times more potent than gemcitabine, the current standard of care for PC.

To determine that AS-10 was selectively toxic to cancer cells, the effect of AS-10 in normal Mouse embryonic fibroblast cells (MEFs) was tested using MTT assay. MEFs were treated with AS-10 for 48 h and the data was compared with Panc-1 cells, treated for 48 h. As shown in FIG. 7B, AS-10 was selectively toxic to PC cells. At the dose which yields 50 percent growth inhibition in PC cells, AS-10 had no effect on MEFs growth. These results support the hypothesis that AS-10 has a large therapeutic window in vitro. Taken together, the data demonstrates that AS-10 was more effective than first line therapy for PC while also being more selective towards PC cells as compared to normal MEFs.

AS-10 Induces G1 and G2 Cells Cycle Arrest

Figure 8:
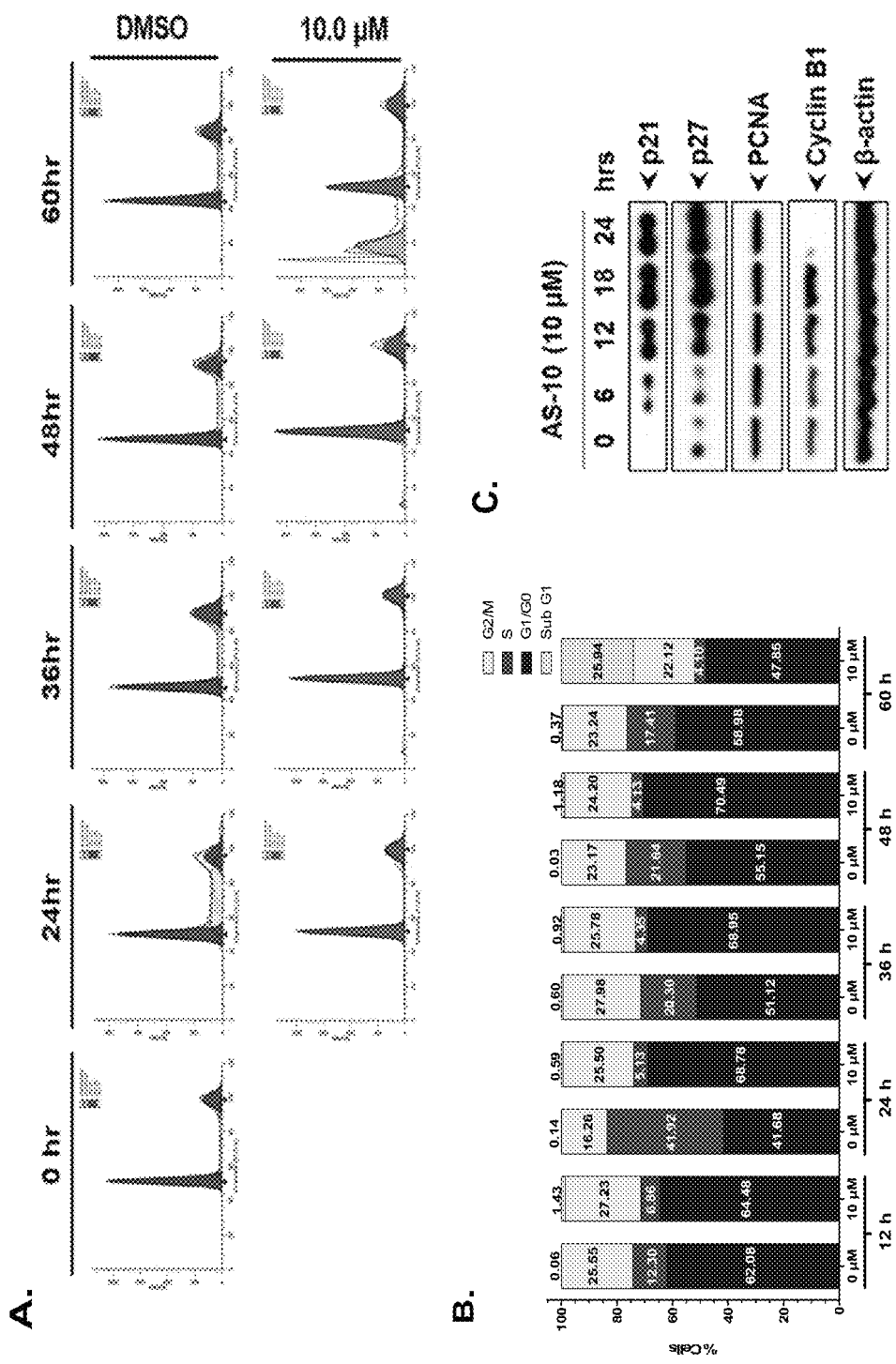
FIG. 8, comprising

The data obtained thus far indicated that AS-10 inhibited colony formation ability and induced growth arrest. The effect of AS-10 on the cell cycle of PC cells was next examined. Panc-1 cells were serum starved for 72 h and then exposed to AS-10 at different doses and time points. At the end of each time point, Panc-1 cells were fixed in cold ethanol and stained with propidium iodide (PI) staining. Stained cells were subjected to cell cycle analysis using flow cytometry. As shown in FIG. 8A, Panc-1 cells treated with AS-10 were not able to transit from G1 phase of cell cycle to synthesis phase (S phase), at any time point tested (24 h to 60 h time points). FIG. 8B represents the quantification of the peaks in FIG. 8A. A consistent cell cycle arrest in G1 and G2/M phase and total inhibition of S phase was observed. In addition, an increase in cell cycle arrest proteins, p21 and p27, was observed (increased in a time-dependent manner starting as early as 6 h for p21 and 12 h for p27), which upon high expression arrests cell cycle in both G1 and G2/M phase (FIG. 8C). Further, an increase in cyclin B1, a marker for G2 phase, was observed, indicating cells arrested in G2 phase of the cell cycle. PCNA expression increases when cells are in S phase of the cell cycle, however in these studies, expression of PCNA did not change, further confirming the absence of S phase when cells are treated with AS-10. Overall, these results support the hypothesis that AS-10 inhibits PC cell growth by arresting cells in G1 and G2/M phase.

AS-10 Induces Apoptotic Cell Death in PC Cells

Activated cell cycle checkpoint proteins inhibit cell cycle and a decision is made inside the cell to either deal with the stress induced by the external agent or to induce apoptosis. The ability of AS-10 to induce apoptosis in PC cells was thus investigated, wherein Panc-1 cells were treated with a dose of 10 µM for indicated time points. Apoptosis was detected by using Muse caspase 3/7 activity assay and Muse Live/Dead annexin V assay. Caspase 3/7 activity assay contains a reagent which is cell permeable and in presence of active caspase 3/7 gets cleaved to a fluorescence molecule. Therefore, cells with caspase 3/7 activity were stained and detected via Muse cell analyzer. One of the hallmarks of apoptosis is the presence of phosphatidylserine (PS) on the outer surface of the plasma membrane. Muse Live/dead kit contains Annexin V dye, which binds to PS on the outer surface of the plasma membrane and detects apoptotic cells. Both assays have a common reagent, 7-ADD, which stains for cells that have lost the integrity of their plasma membrane. Hence, the population of cells which are negative for all three markers (Caspase 3/7 (−), Annexin V (−) and 7-ADD (−)) are healthy cells and show up in the bottom left quadrant of the graph. Cell population which are positive for caspase 3/7 activity or Annexin V and negative for 7-ADD, are considered early apoptotic cells and show up in the bottom right quadrant of the graph. Cell population positive for caspase 3/7, Annexin and 7-ADD show up in the top right quadrant of the graph, which represents cells that died of apoptosis. Cell population which are just positive for 7-ADD and negative for either caspase 3/7 or Annexin V are considered necrotic cells (shown in top left quadrant). As shown in the FIGS. 9A and 9B, upon increasing the exposure time of AS-10 in PC cells, the cell population shifted from bottom left quadrant of the histogram to bottom right quadrant and finally to top left quadrant. The data indicates that upon treatment with AS-10, PC cells die in an apoptotic manner, as detected by the presence of caspase 3/7 activity and Annexin V binding on the outer surface of the plasma membrane. Further, AS-10 did not induce necrosis, as there were no cells detected in the top left quadrant (cells only positive for 7-ADD). Quantification of total apoptotic cells is shown in FIGS. 9C and 9D obtained from Casapse 3/7 activity assay and Annexin V assay, respectively.

Figure 19:
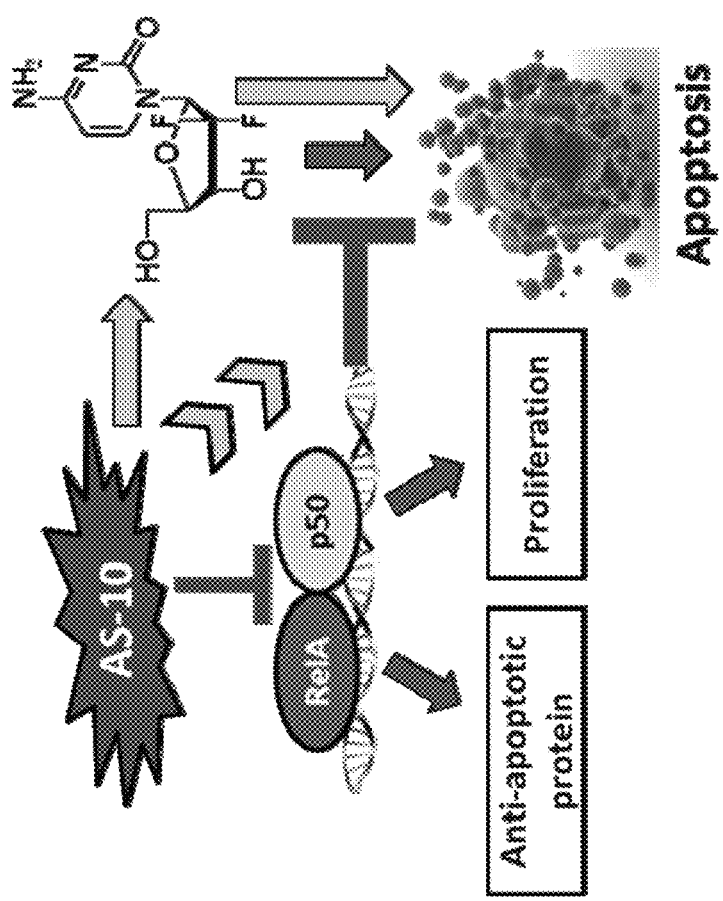
FIG. 19 is a schematic of an exemplary mechanism of action for compound AS-10. AS-10, by its dual role of inhibiting NF-κB and increasing ROS levels, induces apoptosis and further potentiates the apoptotic effects of gemcitabine on Pancreatic cancer cell lines.

The hypothesis that AS-10 induces apoptotic cell death in PC cells was further supported by examining the active caspase 3 (cleaved caspase 3) and its downstream target PARP, a well-known target of caspase 3. In the presence of active caspase 3, PARP gets cleaved and the cleaved PARP can be detected by western blot. As shown in FIG. 9F, with increasing concentration of AS-10, an increase in active caspase 3 (cleaved caspase 3) as well as increase in cleaved PARP was observed. These results are in accordance with the above finding from caspase 3/7 activity assay and Live/dead Annexin V assay. Further, whether the apoptosis induction in presence of AS-10 was mediated through intrinsic or extrinsic apoptotic pathway was also investigated. Cleavage of caspase 9 is a hallmark for intrinsic apoptosis, while cleavage of caspase 8 is the hallmark for extrinsic apoptosis. As shown in FIG. 9E, a profound cleavage of caspase 9 in the presence of AS-10 was observed, however cleaved caspase 8 (active) was not detected. Although not wishing to be bound by any particular theory, this data suggests that in the presence of AS-10, the intrinsic form of apoptosis takes place in PC cells (FIG. 19).

AS-10 Inhibits Activation of NF-κB in Presence of Pro-Inflammatory Stimuli

Inflammation has been shown to be correlated with progression of PC. One of the major inflammatory pathway, NF-κB pathway, is known to be highly expressed in PC tumors and its expression is also related to chemoresistance. Therefore, the effects of AS-10 on the activation of NF-κB in presence of pro-inflammatory stimuli was examined. Panc-1 cells were pre-treated with AS-10 for 6 h and then stimulated with TNF-α 30 minutes prior to termination. In the presence of TNF-α, IKK kinase is activated which phosphorylates IκBα, inhibitory unit of NF-κB, targeting IκBα for degradation. Hence NF-κB (p50-p65 complex) can translocate freely to the nucleus and bind to their DNA binding sites. After pretreatment with AS-10 and stimulation for 30 minutes with TNF-α, PC cells were subjected for nuclear and cytosolic lysis. Nuclear lysates were subjected to electro mobility shift assay (EMSA) using p32 labelled NF-κB binding oligonucleotides, while cytosolic lysates were subjected to Western blot studies, for detection of IκBα. As shown in FIG. 10A, upon stimulation of Panc-1 cells with TNF-α, a prompt band was detected with cell treated with vehicle. However, upon increasing the dose of AS-10, the NF-κB band faded away in a dose dependent manner. This data supports the hypothesis that AS-10 inhibits the binding of NF-κB to its consensus sequences. Further, stimulation of Panc-1 cells with TNF-α induces degradation of IκBα as seen in the FIG. 10B, but upon increasing the dose of AS-10, IκBα is not degraded. Hence, in presence of AS-10 and inflammatory stimuli, NF-κB DNA binding is inhibited and IκBα degradation does not occur.

Both the experiments performed above do not differentiate whether the translocation of NF-κB to the nucleus is inhibited or NF-κB is still translocated to the nuclei but unable to bind to its consensus sequence. Therefore, a microscopy assay was performed. Panc-1 cells were treated for 6 h with AS-10 and stimulated with TNF-α for 30 minutes before termination. Cells were fixed and probed for p-65 protein (part of NF-κB subunit). As shown in FIG. 10D, when vehicle treated cells were stimulated with TNF-α, most of the p-65 was translocated to the nucleus. However, in the presence of AS-10 and TNF-α, p65 is unable to translocate to the nucleus. Therefore, based on the data of these experiments, AS-10 treatment was found to inhibit NF-κB from translocating to the nucleus in presence of inflammatory stimuli. Although not wishing to be bound by any particular theory, these results suggest that AS-10 may be affecting an upstream kinase, such as IKK and hence inhibiting the pathway. Live and dead assays were performed using calcein-AM and ethidium bromide to show whether these effects were due to the presence of dead cells at 6 h time point. An increase in the dead cell population at 6 h time point in presence of AS-10 was not observed (FIG. 10E). Although not wishing to be bound by any particular theory, this results suggests that the effect seen on NF-κB was independent of cell death. AS-10 inhibited the expression of downstream gene target products of NF-κB, Bcl-xL and Mcl-1, in a time dependent manner (FIG. 10F).

Figure 11:
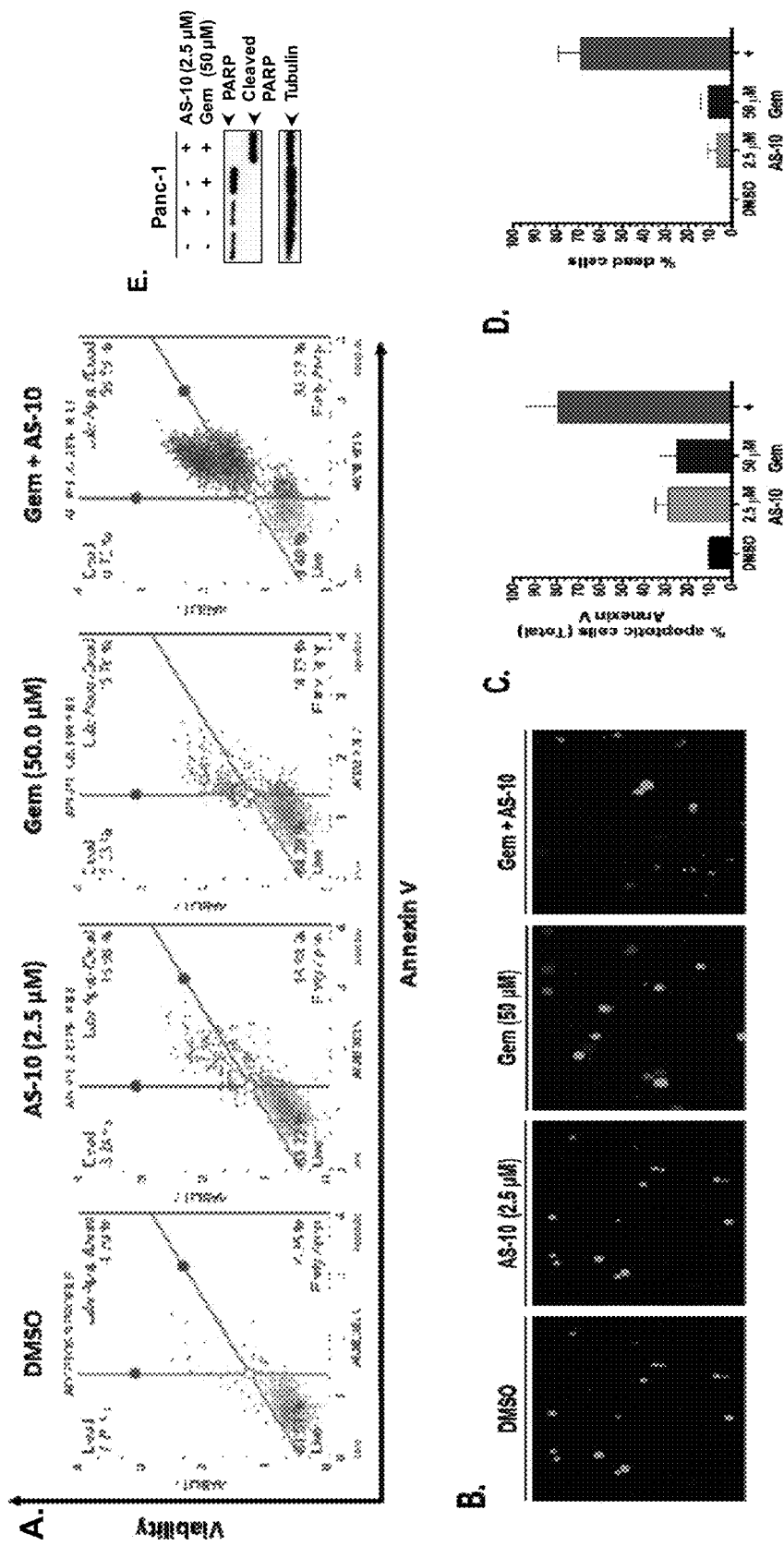
FIG. 11, comprising

AS-10 Potentiates the Anti-Cancer Effects of Gemcitabine, the First Line Therapy for PC The effect of combining AS-10 with gemcitabine on PC cell viability was next examined. The hypothesis was that in presence of AS-10, the NF-κB pathway would be inhibited, thus minimizing gemcitabine resistance. PC cells (Panc-1) were treated with low dose AS-10 (2.5 μM) or gemcitabine (50 μM) for 48 h. After treatment cells were subjected to Live and dead assay using Muse Annexin V assay (FIG. 11A) as well as microscopy live/dead assay using calcein-AM and ethidium bromide (FIG. 11B). Using the Muse Live and dead Annexin V assay (FIGS. 11A and 11C), about ~25% apoptotic cells with either gemcitabine or AS-10 alone were observed, while in combination total apoptotic cells rose to 75%. Further, in microscopy live and dead assay using calcein-AM and ethidium bromide, about ~10% dead cells were detected with gemcitabine or AS-10 treatment alone. However, when treated together in combination, the dead cell count went up to ~75% (FIGS. 11B and 11D). As shown in FIG. 11A, no significant cell population was observed in the top left quadrant (necrotic cell quadrant), indicating that the cell death observed is due to apoptosis. Hence, these results support the hypothesis that AS-10 does indeed potentiate the effects of gemcitabine synergistically when administered together. Results were further confirmed by subjecting the whole cell lysates of the treated cells to Western blot analysis. As shown in FIG. 11E, low dose AS-10 or low dose gemcitabine had no effect on PARP cleavage; however, combination treatment induced PARP cleavage (FIG. 6E). These results further support the data shown in FIGS. 11A-D.

ROS Quencher, NAC, Antagonized AS-10's Anti-Apoptotic Effects on PC Cells.

Figure 12:
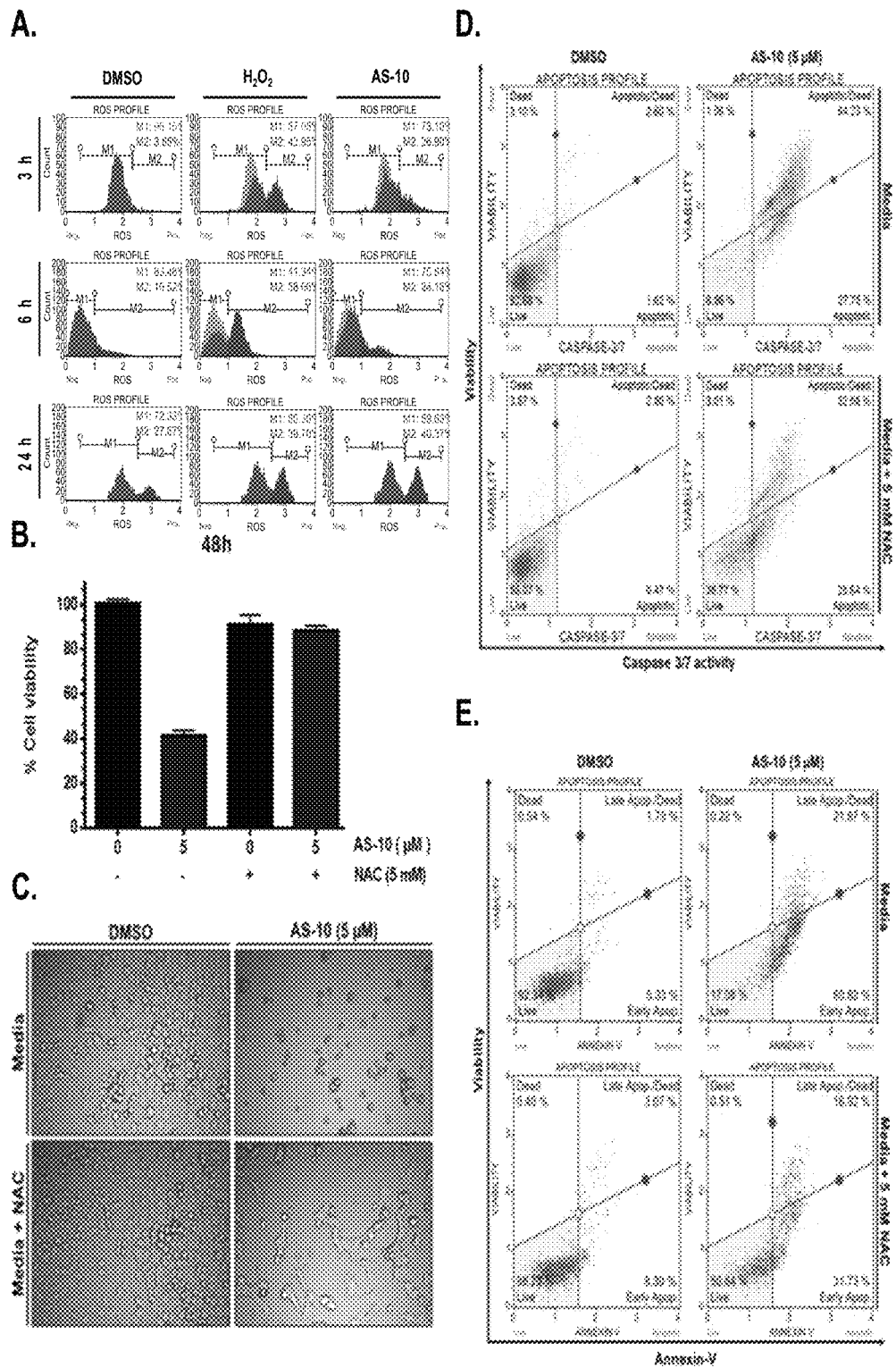
FIG. 12, comprising

Selenium containing compounds are known to increase ROS levels in cancer cells and it has been hypothesized that the effect on cell viability may be due to the compound's ability to generate ROS (Zeng et al., 2014, Che. Asian J. 9:2295-2302; Misra et al., 2015, Nutrients 7:3536-3556). The levels of ROS in AS-10 treated PC cells were measured both at early time points of 3 h and 6 h and a late time point of 24 h. As shown in Figure 12A, AS-10 induced ROS levels by ~23% at all-time points compared to vehicle treated cells. Whether these increases in ROS levels by AS-10 were significant to induce any effects on cell death was further investigated with a ROS quencher, N-acetyl cysteine (NAC), treatment. PC cells were incubated with AS-10, NAC or both for 48 h. After 48 h cells were subjected to MTT assay, Muse Annexin-V staining assay and Muse caspase 3/7 activity assay. As shown in FIG. 12B, MTT results showed that NAC antagonized AS-10's effects and hence, the cell viability was similar to that of control in NAC and AS-10 treated cells. Further, PC cells morphology resembled more to apoptotic cells when treated alone with AS-10, while when treated in combination (AS-10+NAC) PC cell morphology resembled to vehicle treated cells. Muse Annexin-V and Muse Caspase 3/7 activity assays were then performed, as they have been known to be more sensitive than MTT assay. FIGS. 12D and 12E demonstrate that upon addition of NAC, the effect of AS-10 was reduced. Although not wishing to be bound by any particular theory, these results support the hypothesis that ROS induction may have a preliminary role in AS-10 induced cytotoxicity. Therefore, these results suggest that AS-10 has dual function of killing cell death (i) by reducing the pro-survival NF-κB pathway, and (ii) by increasing ROS over time to further activate the apoptotic pathway in PC cells.

AS-10 is Effective Against a Broad Spectrum of Cancer Types

Figure 13:
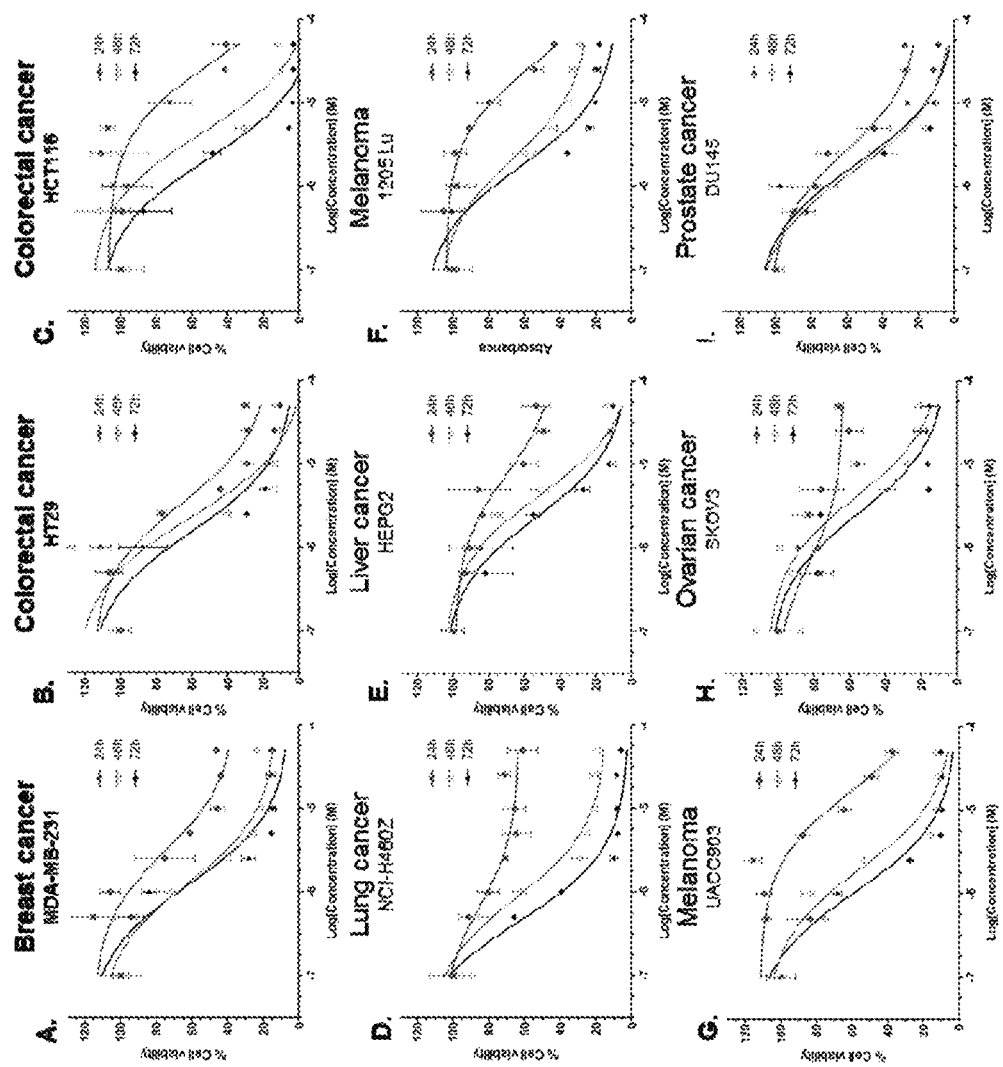
FIG. 13, comprising

AS-10 was further screened using a MTT assay in different cancer cell lines. As shown in FIG. 13, AS-10 also effectively inhibited growth of different cancer cell types such as breast, colorectal, lung, melanoma, ovarian and prostate cancer. AS-10 was more effective towards colon cancer cells followed by prostate, breast, melanoma, liver, and lung cancer. Ovarian cancer cells were the least sensitive cancer cell line towards AS-10 in the panel of cancer cell lines treated.

Furthermore, screening of AS-10 on different prostate cancer cells (LnCAP, PC-3 and DU-145) showed AS-10 to be effective at inducing apoptosis in all prostate cancer cells tested. AS-10 also inhibited the prostate specific antigen (PSA) in cell culture media of LnCAP cells and further down regulated androgen receptor (AR). Although not wishing to be bound by any particular theory, these results suggest that AS-10 may have a potential to be an efficacious chemopreventive agent or therapeutic agent for prostate cancer as well.

AS-10 is Effective in Reducing Cell Growth of all NCI-60 Cell Line Screened

Figure 14:
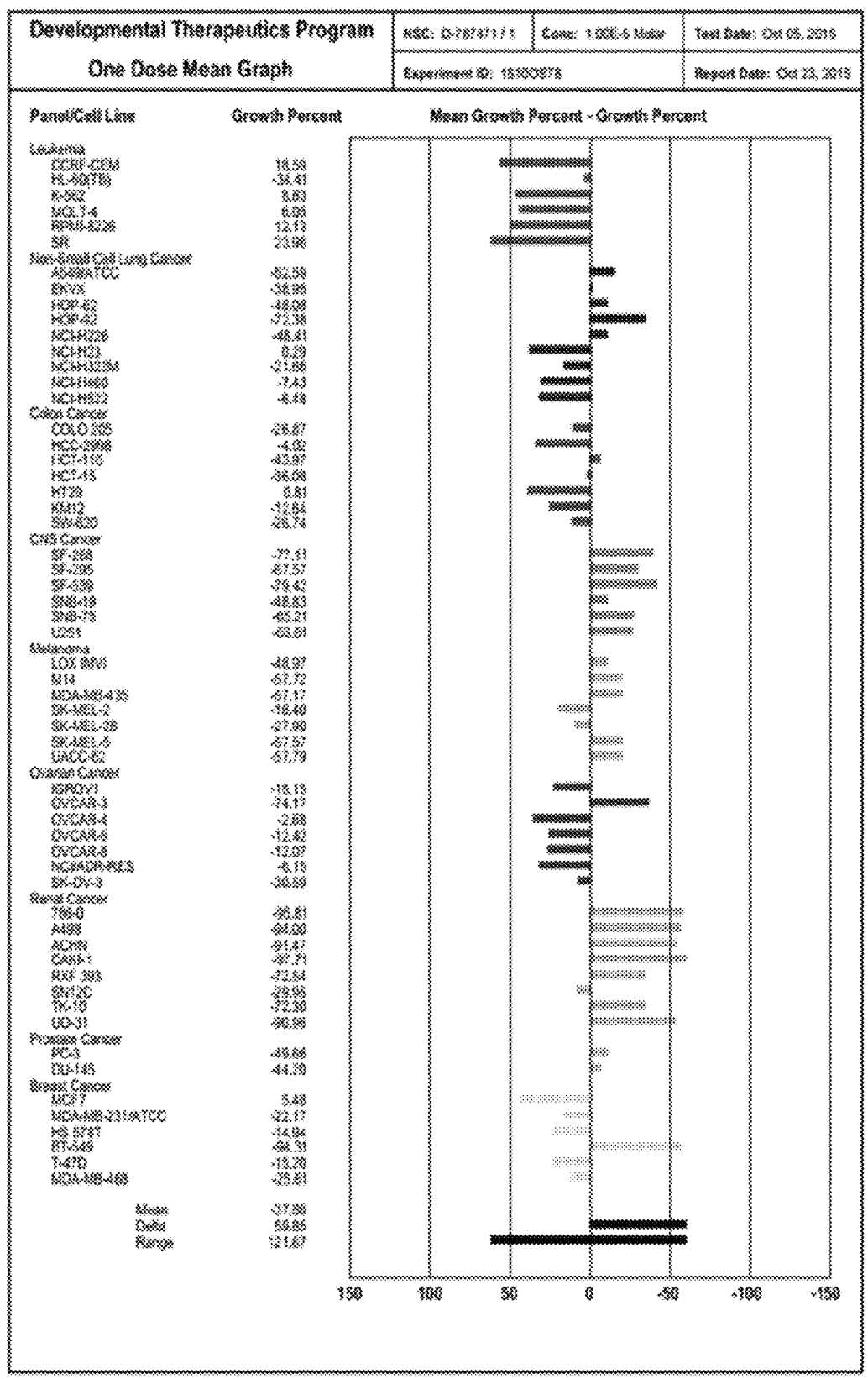
FIG. 14 is a table of experimental data demonstrating that AS-10 is effective on all NCI-60 cell lines tested.
Figure 15:
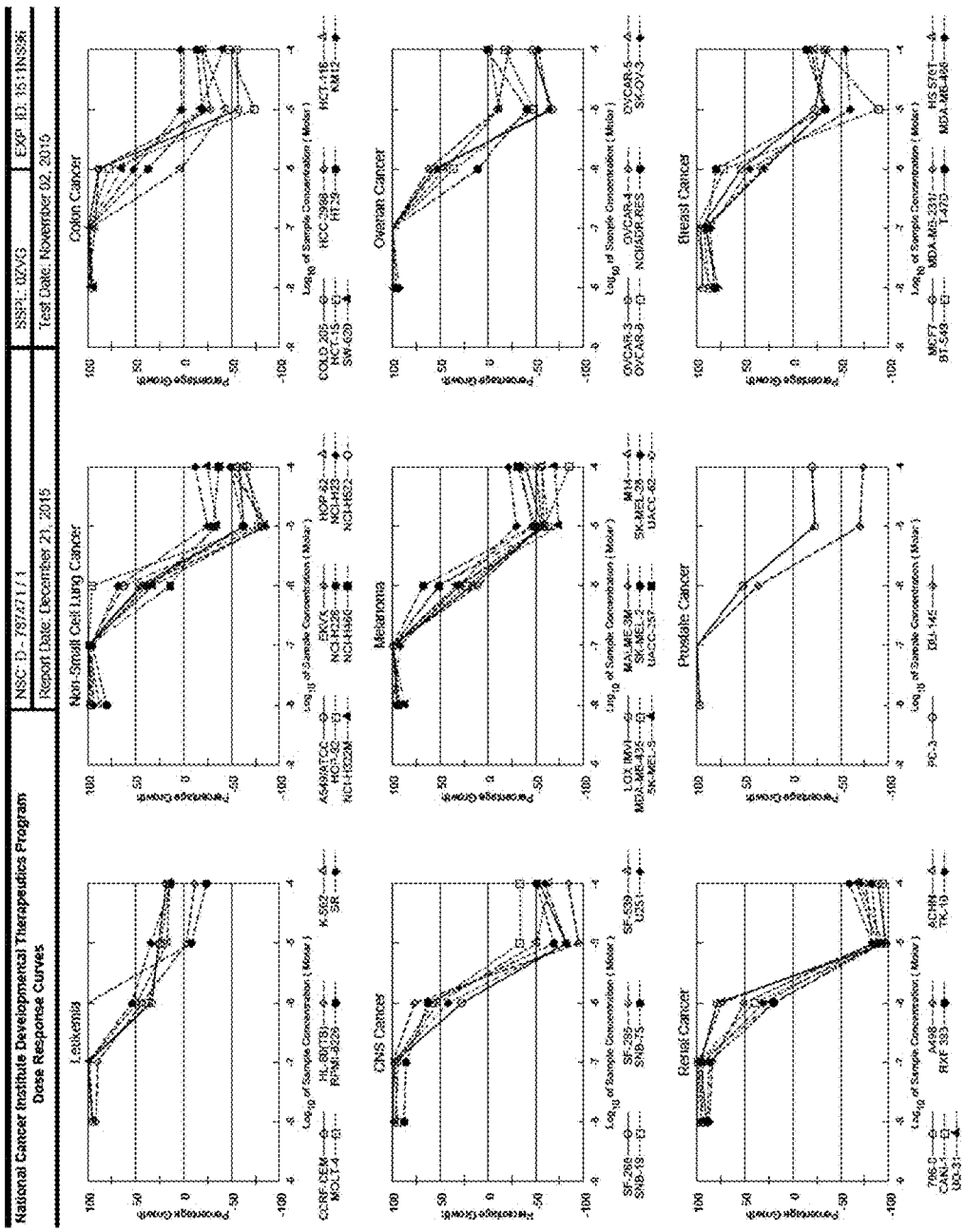
FIG. 15 is series of AS-10 growth curves in different panel of cancer cell lines generated by NCI.
Figure 16:
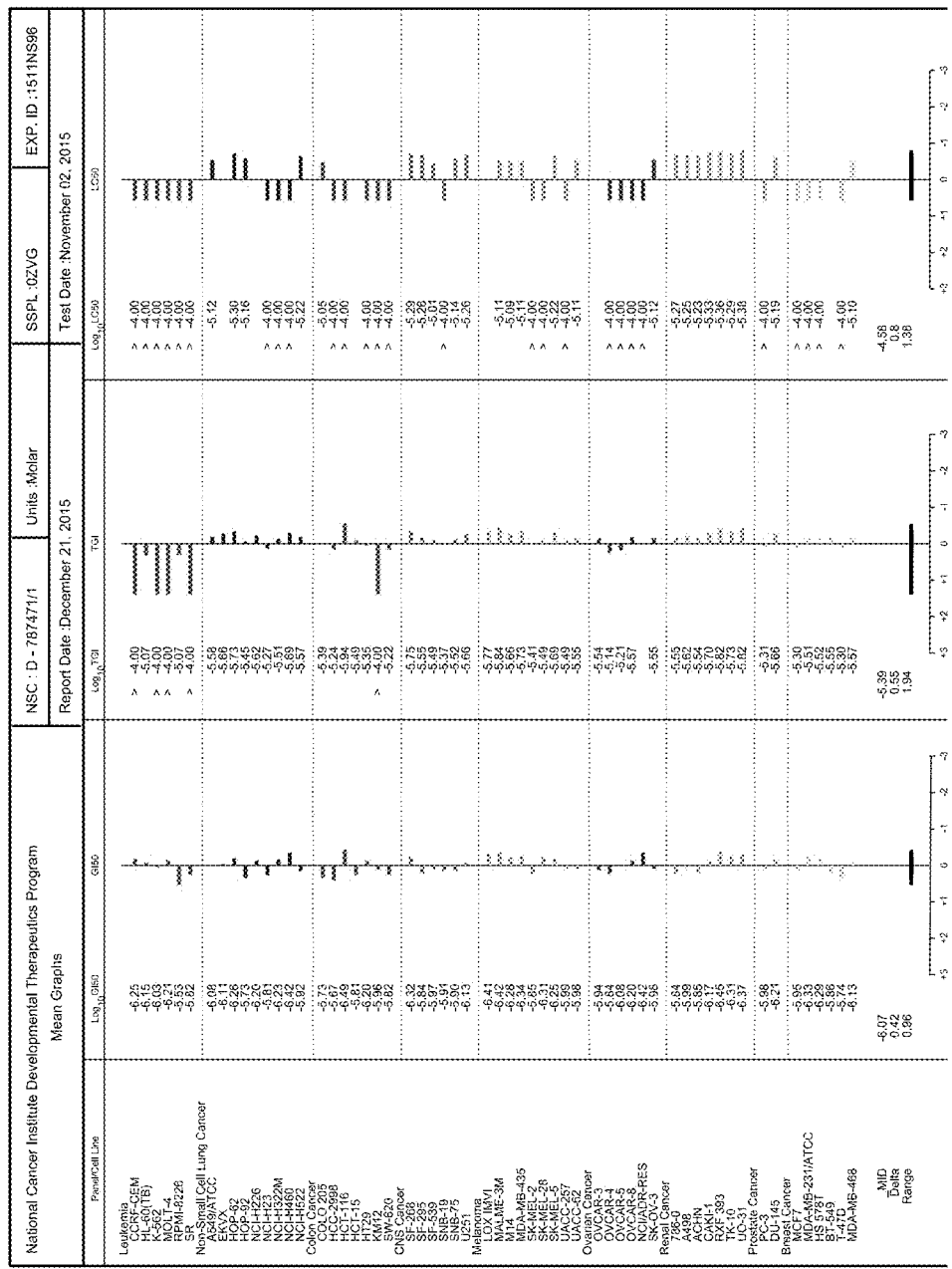
FIG. 16 is a table of experimental data demonstrating that AS-10 is effective on all NCI-60 cell lines tested.
Figure 17:
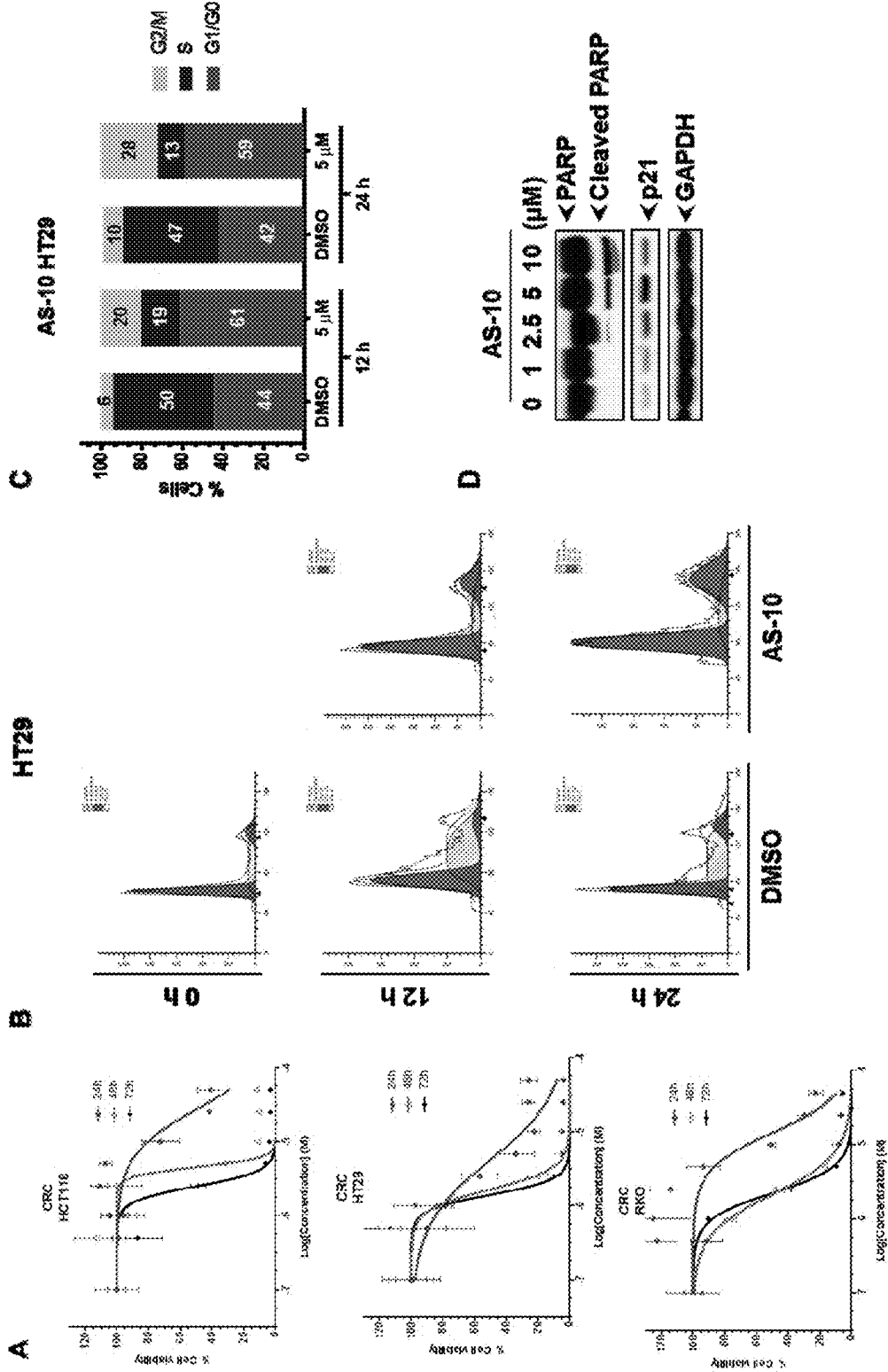
FIG. 17, comprising

AS-10 was submitted for National Cancer Institute's (NCI) Division of Cancer Treatment and Diagnosis (DCTD) for a single dose (10 µM for 72 h) screening on 60 different cancer cell lines (NCI-60 Human Tumor Cell Lines Screen, Developmental Therapeutic Program). The panel of cell lines included leukemia, non-small cell lung, colon, CNS, melanoma, ovarian, renal, prostate and breast cancer cell lines. As shown in FIG. 14, AS-10 inhibited cell growth of all 60 cell lines each to a different extent. Since AS-10 showed to be selectively active, NCI performed the second level of screening, which included multiple doses at single time point. AS-10 was screened against the same 60 cell lines at a dose of 0, 0.01, 0.1, 1, 10 and 100 µM for 72 h. FIG. 15 shows the growth curves of all cancer cell lines tested. Cell lines are grouped by the cancer type they represent. These data clearly demonstrate that AS-10 was selective towards certain cell types, being most cytotoxic towards CNS, melanoma and renal cancer cell lines. FIG. 16 is the tabular format of the effects of AS-10 on growth of all the tested cell lines.

Maximum tolerated dose (MTD) studies were conducted in nude mice and found to be ~80 mg/kg body weight [intraperitoneal (IP) injection, 3 times/week)].

AS-10 Inhibited Subcutaneous Tumor Growth in a Colon Cancer Xenograft Mouse Model Athymic nude mice were used to evaluate the tumor inhibitory effect of AS-10 against a xenograft model of colon cancer. Approximately, $5 \times 10^6$ cells (HCT116) were inoculated into both left and right flanks of mice. After eight days, vehicle (DMSO) or AS-10 (45.2 mg/Kg) were injected via IP injection three times per week for 18 days. As shown in FIG. 20, AS-10 effectively inhibited tumor growth (~70% inhibition compared to vehicle treated mice). Body weights of mice indicated no apparent no systemic toxicity. Although not wishing to be bound by any particular theory, the data obtained from these studies suggests that AS-10 effectively inhibits tumor growth without any apparent toxicity.

Drug-Likeness of AS-10

In silico evaluation show that AS-10 has c Log P 2.2 and MW 473, and therefore fits into the requirements of Lipinski's Rule-of-Five, formulated to determine the drug-likeness of a small molecule.

Figure 18:
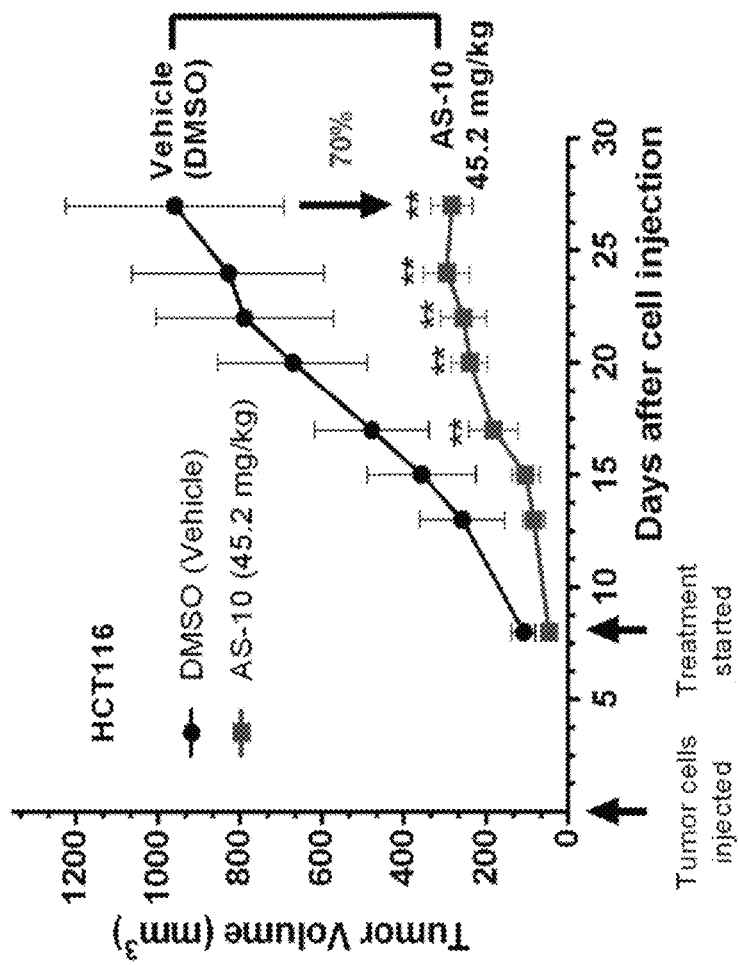
FIG. 18 depicts experimental data of tumor inhibition studies. Athymic nude mice were used to evaluate the inhibitory effect of AS-10 (45.2 mg/kg; IP; three times a week) against a xenograft model of colon cancer. The experimental data demonstrates that AS-10 inhibited tumor growth by ~70%.

AS-10 Inhibited Subcutaneous Tumor Growth in a Colon Cancer Xenograft Mouse Model Athymic nude mice were used to evaluate the tumor inhibitory effect of AS-10 against a xenograft model of colon cancer. Approximately, $5 \times 10^6$ cells (HCT116) were inoculated into both left and right flanks of mice. After eight days, vehicle (DMSO) or AS-10 (45.2 mg/Kg) were injected via IP injection three times per week for 18 days. As shown in FIG. 18, AS-10 effectively inhibited tumor growth (~70% inhibition compared to vehicle treated mice). Body weights of mice indicated no apparent no systemic toxicity. Although not wishing to be bound by any particular theory, the data obtained from these studies suggests that AS-10 effectively inhibits tumor growth without any apparent toxicity.

AS-10 was identified as a result of extensive SAR studies focused toward developing an effective small molecule for PC therapy. The chemical composition of AS-10 consists of a selanazolidine ring flanked by to acetyl salicylate (aspirinyl) functionalities leading to a unique compound that is selectively toxic to PC cells. AS-10 was more effective than aspirin in killing cancer cells. This data suggests that lower dose requirements of AS-10 will address GI toxicity issues.

In screening results, AS-10 potently inhibited PC growth, while at similar doses ASA did not have any effects on these cancer cell lines. Colony formation assay tests the growth inhibitory activity of a compound over a long period of time. Therefore, Panc-1 cells pre-treated with AS-10, were subjected to colony formation assay in absence of AS-10 over a period of 17 days. AS-10 pre-treated Panc-1 cells had lost their ability to proliferate. Further, the data described herein demonstrates that AS-10 is more effective at reducing cell viability of cancer cells compared to normal MEFs, showing that AS-10 has more selectivity towards cancer cell over normal cells, and should result in minimal systemic toxicity.

It is noteworthy that the current therapies, including first line therapeutic gemcitabine, are associated with serious side effects. The effects of AS-10 were compared to gemcitabine. The data described herein shows that AS-10 is more effective at reducing PC cell viability than gemcitabine. Gemcitabine is a nucleoside that exhibits its toxicity via DNA damage and hence it is toxic to most highly proliferative normal cells (Plunkett et al., 1995, Semin. Oncol. 22:3-10). These results demonstrate that AS-10 is an improvement over gemcitabine as it is not only significantly more potent, but is selective towards cancer cells.

The growth inhibition ability of AS-10 was also investigated by performing cell cycle studies of PC cells treated with AS-10. The results indicate that AS-10 induces $G1/G_0$ and G2/M phase cell cycle arrest. At later time points there was an increase in sub $G_0$ peak indicative of apoptotic cells. Since ASA has been known to have multiple effects in cancer cells (Dovizio et al., 2012, Pharmaceuticals 5:1346-1371), these results suggests that AS-10 may also affect different pathways to inhibit PC growth. AS-10 up-regulated the cell cycle arrest markers such as p21 and p27, which indicates the activation of DNA checkpoint markers in both G1 and G2/M phase. This marker is activated in the presence of DNA damage or apoptosis (Gartel and Tyner, 2002, Mol. Cancer Ther. 1:639-649; Abbas and Dutta, 2009, Nat. Rev. Cancer 9:400-414; Kastan and Bartek, 2004, Nature 432: 316-323).

Figure 9:
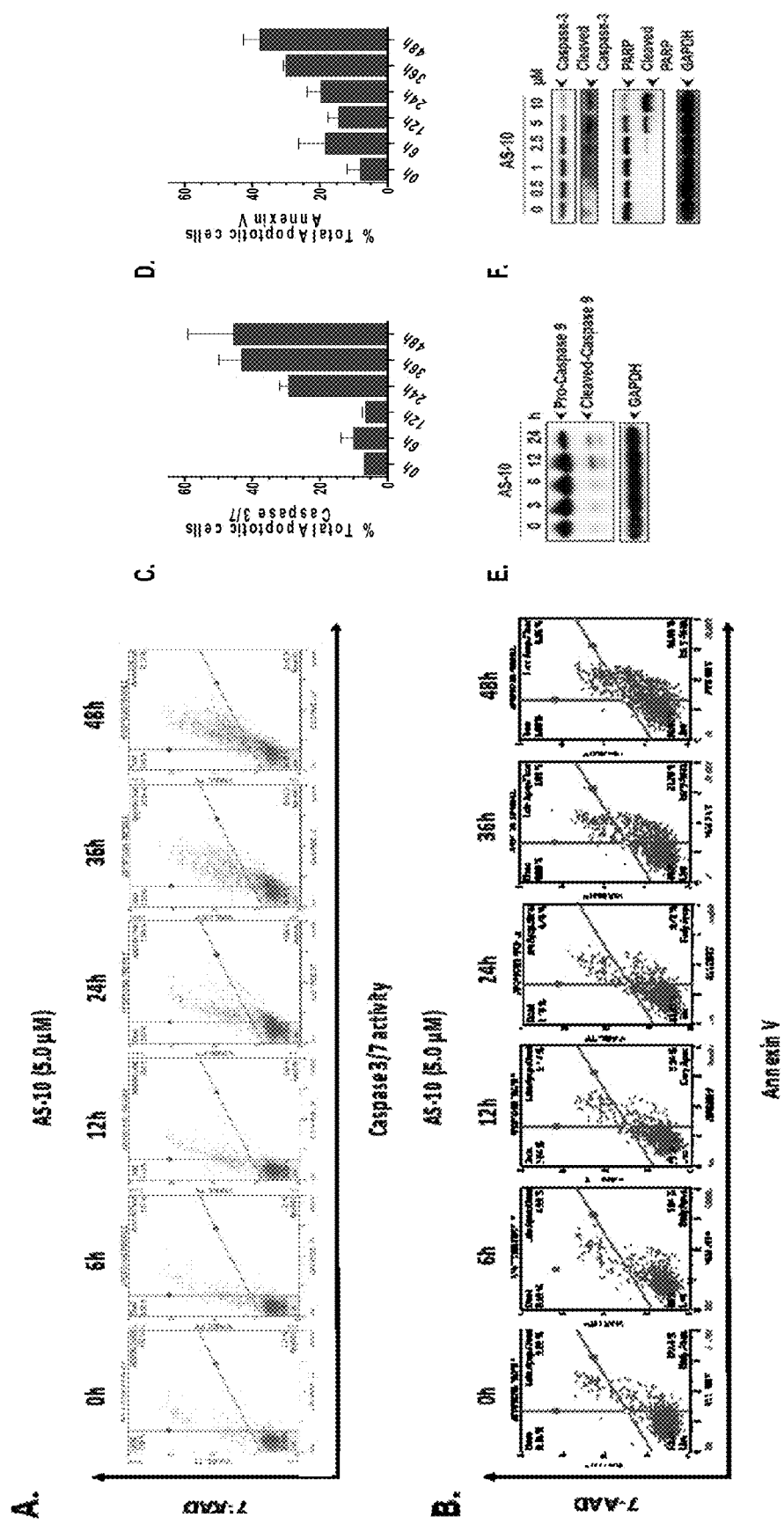
FIG. 9, comprising

The downstream effect of cell cycle inhibition, which is apoptosis or senescence, was also examined. The data described herein shows that AS-10 induced apoptotic death in PC cells. The apoptotic pathway can be activated via extrinsic or intrinsic apoptotic signals (Taylor et al., 2008, Nat. Rev. Mol. Cell Biol. 9:231-241). Activation of caspase 8 is a hallmark of extrinsic apoptotic pathway activation mediated by activation of death receptors, while activation of caspase 9 is a hallmark of intrinsic apoptotic pathway activation mediated by mitochondrial mediated death pathway (Taylor et al., 2008, Nat. Rev. Mol. Cell Biol. 9:231-241). In the described Western blot studies, caspase 8 was never activated; however AS-10 was able to activate caspase 9, as indicated by the cleavage of pro-caspase 9. Further, caspase 3 activation was detected and at the same concentration of AS-10, the down-stream target of caspase 3, PARP was also cleaved in the presence of AS-10 (FIG. 9).

One of the common mechanisms of action of ASA and most selenium compounds is inhibition of pro-inflammatory NF-κB pathway (Kopp and Ghosh, 1994, Science 265:956-959). Therefore, the effects of AS-10 on NF-κB activation in presence of inflammatory stimuli like TNF-α were investigated. As shown in an EMSA assay, in the presence of inflammatory stimuli, NF-κB binds to its consensus DNA sequence and a strong band shift in the vehicle treated Panc-1 cells is observed. However, when the dose of AS-10 is increased in cells stimulated with TNF-α, NF-κB associated lagging/shifting band disappears. These results demonstrate that AS-10 has the ability to inhibit NF-κB-DNA binding. Further, Western blot analysis of the cytosolic lysates of Panc-1 cells revealed that IκBα was degraded in presence of inflammatory stimuli; however in the presence of AS-10, the degradation of IκBα was inhibited. Further, to confirm whether the restoration of IκBα leads to inhibition of NF-κB translocation to the nuclei, confocal microscopy was performed to look at the translocation patterns of p65 (a subunit of NF-κB) in the presence of inflammatory stimuli and AS-10. The confocal microscopy results distinctly demonstrated that in presence of AS-10 and inflammatory stimuli, p65 was unable to translocate to the nuclei. Taken together, based on results from EMSA, Western blot, and confocal microscopy assays, these results demonstrate that AS-10 is able to prevent the activation of NF-κB pathway in presence of inflammatory stimuli.

Figure 10:
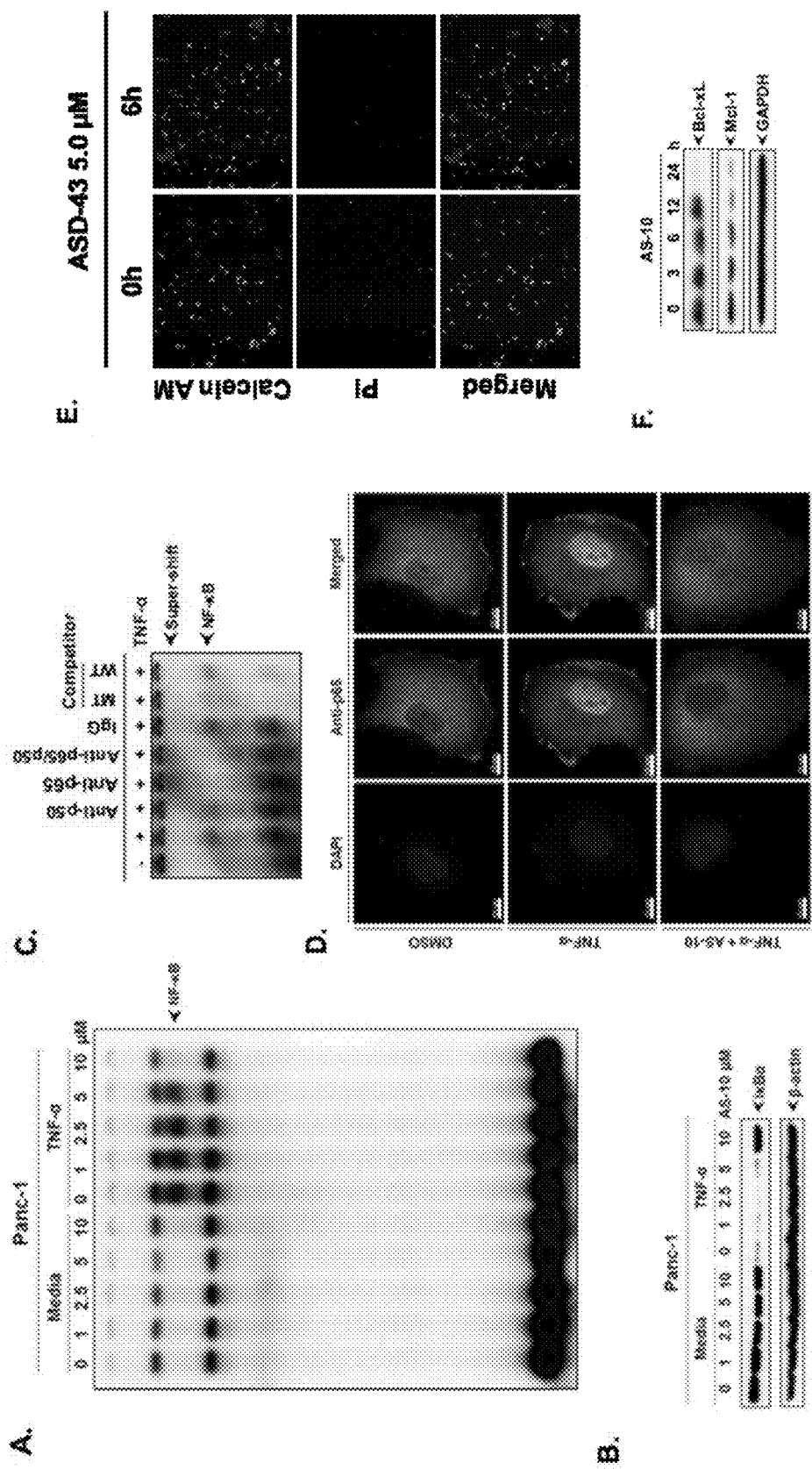
FIG. 10, comprising

The results described herein also demonstrate that AS-10 has the ability to inhibit NF-κB activation in presence of inflammatory stimuli, as well as to sensitize PC cells towards gemcitabine treatment (FIG. 10).

Furthermore, AS-10 was observed to induce ROS in PC cells by about 20%. The contribution that this ~20% increase in ROS levels may have on anti-cancer activity of AS-10 was further investigated by examining the anti-cancer effects of AS-10 in presence of ROS quencher, NAC. The data shows that AS-10 partially lost its activity in presence of a ROS quencher. Although not wishing to be bound by any particular theory, these results suggest that AS-10 is has the ability to increase ROS. The data further demonstrates that AS-10 has a dual effect of increasing ROS and inhibition of NF-κB pathway, since quenching ROS only partially reduced its anti-cancer activity.

Both ASA and selenium containing compounds can inhibit activity of IKK kinase, by either competing with ATP at the activation cite or by covalently binding and inhibiting the activation loop (Gasparaian et al., 2002, Mol. Cancer Ther. 1:1079-1087). Acetylation of the threonine amino acid inside IKK activation loop can inhibit its activity (Mittal et al., 2006, Proc. Natl. Acad. Sci. USA 103:18574-18579). Although not wishing to be bound by any particular theory, if the acetyl groups in AS-10 behave in a similar manner, then IKK may be a potential target of AS-10 for this pathway. Additionally, restoration of IκBα levels as shown in the Western blot analyses described herein suggests that either IKK kinase activity or proteasomal activity has been inhibited by AS-10. Moreover, AS-10 also downregulated the NF-κB target proteins like Bcl-xL and Mcl-1, and hence making cells sensitive towards cell death stimuli.

Example 2: AS-10 Suppresses Androgen Receptor Signaling and Induces Apoptosis of LNCaP Prostate Cancer Cells Aspirin as the best known low cost Non-Steroidal Anti-inflammatory drug (NSAID) has been associated with lowering risk of colorectal cancer, in addition to its cardiovascular health benefit at low dose (baby Aspirin) and over-the-counter pain medication. AS-10 has been found to be a novel aspirin-selenium compound with promising anti-cancer drug-like properties in terms of potency enhancement, selective cytotoxicity against cancer cells including majority of NCI-60 panel, while sparing normal mouse embryonic fibroblasts in cell culture screening assays. Preliminary toxicology study in mice had shown a wide safety margin. Extensive structure-activity relationship investigation suggested a novel structural basis, instead of releasable selenium, that accounted for the striking potency. To investigate the potential chemopreventive attributes of AS-10 against prostate carcinogenesis, LNCaP cells (wild type p53, functional androgen receptor, AR) were selected to examine the growth suppression and apoptosis responses in cell culture. The rationale for choosing LNCaP cell line as target cells is based on data demonstrating that precancerous prostatic lesions that are the intended targets of chemoprevention as well as early stage prostate cancer retain wild type p53 and they are critically dependent on AR signaling for survival. The results described herein show that cell viability (MTT) test detected a potent growth inhibition of LNCaP cells in a time and concentration dependent manner, with an $EC_{50}$ in range of 1.7 to 2.5 μM range compared with aspirin in the millimolar range. Western blot analysis of AS-10 treated LNCaP cells showed decreased protein level of AR and its best known downstream target prostate specific antigen (PSA) in a concentration-dependent manner. In addition, AS-10 treatment led to increased Annexin V staining, caspase 3/7 activity, and PARP cleavage, all indicators of caspase-mediated apoptosis. Furthermore, AS-10 treatment increased the expression of p53-DNA damage response (DDR) proteins such as p21 (canonical target of p53) and p-H2A.X (a marker for DNA strand breaks). It was hypothesized that ROS generation may be involved in LNCaP cells to trigger the DDR and apoptosis responses. Although not wishing to be bound by any particular theory, these results support the hypothesis that AS-10 is useful as a chemopreventive agent for prostate carcinogenesis.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound selected from the group consisting of:

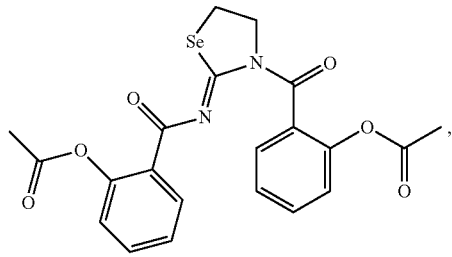 [SMILES: CC(=O)Oc1ccccc1C(=O)/N=C1\[Se]CCN1C(=O)c1ccccc1OC(C)=O]

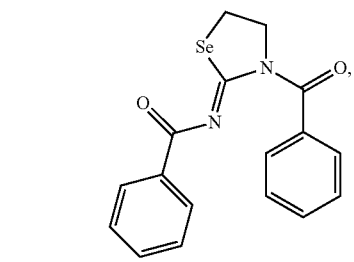

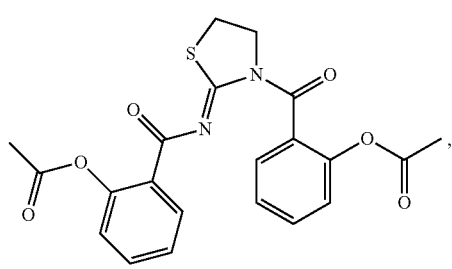

-continued

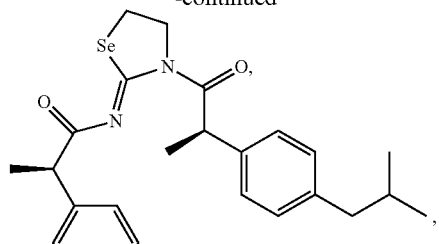

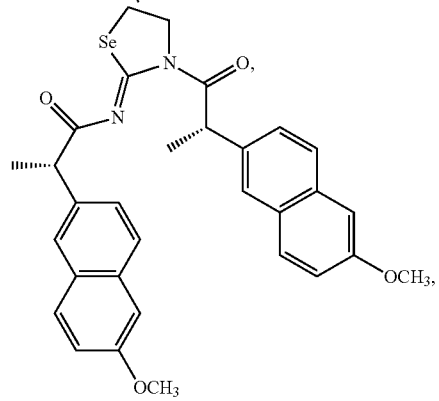

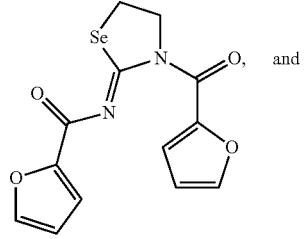

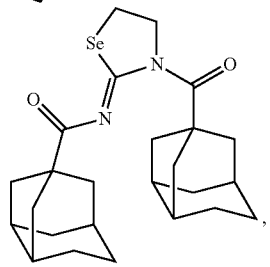

and

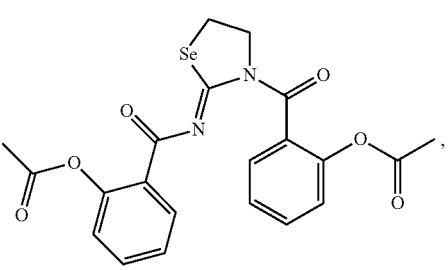

a salt or solvate thereof, and any combinations thereof.

2. The compound of claim 1, wherein the compound is:

a salt or solvate thereof, and any combinations thereof.

3. A composition comprising a compound of claim 1.

4. The composition of claim 3, wherein the composition further comprises a pharmaceutically acceptable carrier.

5. The composition of claim 3, wherein the composition further comprises an additional therapeutic agent.

6. The composition of claim 5, wherein the therapeutic agent is gemcitabine.

* * * * *